US010025774B2

(12) United States Patent
Coulet et al.

(10) Patent No.: US 10,025,774 B2
(45) Date of Patent: Jul. 17, 2018

(54) METHOD AND SYSTEM FOR EXTRACTION AND NORMALIZATION OF RELATIONSHIPS VIA ONTOLOGY INDUCTION

(75) Inventors: Adrien Coulet, Nancy (FR); Nigam H. Shah, Menlo Park, CA (US); Yael Garten, Mountain View, CA (US); Mark Musen, Palo Alto, CA (US); Russ B. Altman, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 13/481,808

(22) Filed: May 26, 2012

(65) Prior Publication Data
US 2013/0073571 A1 Mar. 21, 2013

Related U.S. Application Data

(60) Provisional application No. 61/491,103, filed on May 27, 2011.

(51) Int. Cl.
*G06F 7/00* (2006.01)
*G06F 17/27* (2006.01)
*G06F 19/28* (2011.01)

(52) U.S. Cl.
CPC .......... *G06F 17/2785* (2013.01); *G06F 19/28* (2013.01)

(58) Field of Classification Search
CPC ............... G06F 19/24; G06F 19/707; G06F 2221/0717; G06F 2221/072; G06F 17/2785; G06F 19/28

USPC .......... 707/771, 755, 808, 999.101
See application file for complete search history.

(56) References Cited

U.S. PATENT DOCUMENTS

| | | | |
|---|---|---|---|
| 7,493,253 B1 * | 2/2009 | Ceusters et al. | 704/9 |
| 7,953,593 B2 * | 5/2011 | Marchisio et al. | 704/9 |
| 8,050,870 B2 | 11/2011 | Heckerman et al. | |
| 8,321,196 B2 * | 11/2012 | Hale et al. | 704/2 |
| 8,433,715 B1 * | 4/2013 | Mirhaji | 707/756 |
| 2006/0074836 A1 * | 4/2006 | Gardner et al. | 706/60 |
| 2008/0162541 A1 * | 7/2008 | Oresic et al. | 707/102 |

(Continued)

OTHER PUBLICATIONS

Adrien Coulet, Yael Garten, Michel Dumontier, Russ B Altman, Mark A Musen, Nigam H Shah, Integration and publication of heterogeneous text-mined relationships on the Semantic Web, From Bio-Ontologies 2010: Semantic Applications in Life Sciences Boston, MA, USA, Jul. 2010.*

(Continued)

*Primary Examiner* — Mohammed R Uddin
(74) *Attorney, Agent, or Firm* — KPPB LLP

(57) ABSTRACT

Methods for developing an ontology of pharmacogenomics (PGx) relationships starting from a lexicon of key pharmacogenomic entities and a syntactic parse is described. The syntactic structure of PGx statements is used to systematically extract commonly occurring relationships and to map them to a common schema. In an embodiment, extracted relationships have a 70-87.7% precision and involve not only key PGx entities such as genes, drugs, and phenotypes (e.g., VKORC1, warfarin, clotting disorder), but also critical entities that are frequently modified by these key entities (e.g., VKORC1 polymorphism, warfarin response, clotting disorder treatment).

33 Claims, 16 Drawing Sheets

(56) References Cited

U.S. PATENT DOCUMENTS

| | | | |
|---|---|---|---|
| 2009/0012842 A1* | 1/2009 | Srinivasan et al. | 705/10 |
| 2011/0087670 A1* | 4/2011 | Jorstad et al. | 707/741 |
| 2012/0011170 A1* | 1/2012 | Elad et al. | 707/804 |
| 2012/0290288 A1* | 11/2012 | Ait-Mokhtar | 704/9 |
| 2013/0073217 A1 | 3/2013 | Dewey et al. | |
| 2013/0080069 A1 | 3/2013 | Cordero et al. | |
| 2013/0080365 A1 | 3/2013 | Dewey et al. | |
| 2013/0090908 A1 | 4/2013 | Dewey et al. | |
| 2013/0090909 A1 | 4/2013 | Dudley et al. | |
| 2014/0088942 A1 | 3/2014 | Li et al. | |

OTHER PUBLICATIONS

Towards pharmacogenomics knowledge discovery with the semantic web, Michel Dumontier and Natalia Villanueva-Rosales, Nov. 2008.*

"Discovering New Drug—Drug Interaction by Text-Mining the Biomedical Literature", Bethany Percha, Department of Biomedical Informatics, Stanford University, Stanford, CA, Winter 2011.*

Agichtein et al., "Snowball: extracting relations from large plaintext collections", In: ACM DL; 2000. p. 85-94.

Ahlers et al., "Extracting semantic predications from MEDLINE citations for pharmacogenomics", In: Pacific Symposium on Biocomputing; 2007, pp. 209-220.

Aussenac-Gilles et al., "Text analysis for ontology and terminology engineering", Appl Ontol 2005;1(1):35-46.

Baader et al., The description logic handbook, Cambridge University Press; 2003, 574 pgs.

Blaschke et al., "Automatic extraction of biological information from scientific text: protein-protein interactions", In: ISMB; 1999. p. 60-67.

Buitelaar et al., "Ontology learning from text: methods, evaluation and applications", vol. 123 of Frontiers in Artificial Intelligence and Applications, IOS Press; 2005, 4 pgs.

Ciaramita et al., "Unsupervised learning of semantic relations between concepts of a molecular biology ontology", In: IJCAI; 2005. p. 659-664.

Cilibrasi et al., "Automatic meaning discovery using Google", In: Kolmogorov complexity and applications; 2006, 31 pgs.

Cohen et al., "Empirical distributional semantics: methods and biomedical applications", J Biomed Inform 2009;42(2):390-405.

Coulet et al., "Suggested ontology for pharmacogenomics (SO-pharm): modular construction and preliminary testing", In: KSinBIT; 2006, LNCS 4277. p. 648-657.

Crowley, "Ontology Development Information Extraction (ODIE) project", http://www.bioontology.org/ODIE-project, [accessed Feb. 11, 2010], 2 pgs.

De Marneffe et al., "The stanford typed dependencies representation", In: COLING workshop on cross-framework and cross-domain parser evaluation; 2008, 8 pgs.

Dumontier et al., "Towards pharmacogenomics knowledge discovery on the semantic web", Briefings Bioinform 2009;10(2):153-63.

Friedman et al., Genies: a natural-language processing system for the extraction of molecular pathways from journal articles, In: ISMB (supplement of bioinformatics); 2001. p. 74-82.

Fundel et al., "Relex—relation extraction using dependency parse trees", Bioinformatics 2007;23(3):365-71.

Garten et al., "Pharmspresso: a text mining tool for extraction of pharmacogenomic concepts and relationships from full text", BMC Bioinformatics 2009; 10 (S-2).

Gupta et al., "Using ontologies and the web to learn lexical semantics", In: IJCAI; 2007. p. 1618-1623.

Hunter et al., "OpenDMAP: an open-source, ontology-driven concept analysis engine, with applications to capturing knowledge regarding protein transport, protein interactions and cell-type-specific gene expression", BMC Bioinformatics 9(78), 22 pgs.

Klein et al., "Accurate unlexicalized parsing", In: ACL; 2003. p. 423-30.

Klein et al., "Integrating genotype and phenotype information: an overview of the PharmGKB project", Pharmacogenomics J 2001;1(3):167-70.

Knublauch et al., "The Protege OWL plugin: an open development environment for semantic web applications", In: ISWC; 2004. p. 229-243.

Li et al., "Building disease-specific drug-protein connectivity maps from molecular interaction networks and PubMed abstracts", PLoS Comput Biol 2009;5(7):e1000450+.

Rindflesch et al., "Semantic relations asserting the etiology of genetic diseases", In: AMIA Annu Symp Proc 2003; 2003., p. 554-558.

Rosario et al., "Classifying semantic relations in bioscience texts", In: ACL; 2004. p. 430-437.

Saric et al., "Extraction of regulatory gene/ protein networks from MEDLINE", Bioinformatics 2006;22(6):645-650.

Tari et al., "Querying parse tree database of MEDLINE text to synthesize user-specific biomolecular networks", In: Pacific symposium on biocomputing; 2009. p. 87-98.

Tsujii, "In: Proceedings of the BioNLP 2009 workshop companion volume for shared task", 2009, 142 pgs.

Wermter et al., "You can't beat frequency (unless you use linguistic knowledge)—a qualitative evaluation of association measures for collocation and term extraction", In: ACL; 2006.

Xu et al., "Unsupervised method for automatic construction of a disease dictionary from a large free text collection", In: AMIA Annu Symp Proc 2008; 2008. p. 820-824.

Ashley et al., "Clinical assessment incorporating a personal genome", Lancet, May 1, 2010, 375(9725): p. 1525-35, Pmcid: 2937184, www.thelancet.com.

Bezemer et al., "no. association between the common Mthfr 677C-T polymorphism and venous thrombosis: results from the Mega study", Arch Intern Med 167, 497-501, 2007.

Broman et al., "Comprehensive human genetic maps: individual and sex-specific variation in recombination", Am J Hum Genet 63, Aug. 7, 1998, pp. 861-869.

Coop et al., "High-resolution mapping of crossovers reveals extensive variation in fine-scale recombination patterns among humans", Science, vol. 319, 1395-1398, Mar. 7, 2008.

Coulet et al., ""Integration and publication of heterogeneous text-mined relationships on the Semantic Web"," From Bio-Ontologies 2010: Semantic Applications in Life Sciences, Boston, MA, USA, Jul. 9-10, 2010, http://www.jbiomedsem.com/content/2/S2/S10, 16 pgs.

De Bakker et al., "A high-resolution HLA and SNP haplotype map for disease association studies in the extended human MHC", Nat Genet 38, Oct. 2006, pp. 1166-1172.

Degner et al., "Effect of read-mapping biases on detecting allele-specific expression from RNA-sequencing data", Bioinformatics, vol. 25, No. 24, Oct. 6, 2009, pp. 3207-3212.

Dewey et al., "Phased Whole-Genome Genetic Risk in a Family Quartet Using a Major Allele Reference Sequence", PLoS Genetics, Sep. 2011, vol. 7, Issue 9, 15 pgs.

Dudley et al., "Evolutionary Meta-Analysis of Association Studies Reveals Ancient Constraints Affecting Disease Marker Discovery", Mol. Biol. Evol. 29(9): 2087-2094, 2012.

Durbin et al., "A map of human genome variation from population-scale sequencing", Nature 467, 1061-1073, Oct. 28, 2010.

Eyre-Walker, "An analysis of codon usage in mammals: selection or mutation bias?", J. Mol. Evol., May 13, 1991, vol. 33, pp. 442-449.

Feldman et al., "Selective changes in cardiac gene expression during compensated hypertrophy and the transition to cardiac decompensation in rats with chronic aortic banding", Circ Res. 1993; vol. 73, No. 1, pp. 184-192.

Fitch, "Toward Defining the Course of Evolution: Minimum Change for a Specific Tree Topology", Systematic Zoology, Dec. 1971, vol. 20, No. 4, pp. 406-416.

Green et al., "Disclosure of APOE Genotype for Risk of Alzheimer's Disease", The New England Journal of Medicine, vol. 361, No. 3, Jul. 16, 2009, pp. 245-254.

Grier et al., "Quantification of Hox and surfactant protein-B transcription during murine lung development", Neonatology. 2009; vol. 96, pp. 50-60.

(56) References Cited

OTHER PUBLICATIONS

Grinberg et al., "The ZIC gene family in development and disease", Clin Genet. 2005; 67:290-296.
Kimura, Motoo, "Evolutionary rate at the molecular level", Nature, Feb. 17, 1968, vol. 217, pp. 624-626.
Klein, et al., "Estimation of the Warfarin Dose with Clinical and Pharmacogenetic Data", New England Journal of Medicine, vol. 360, 753764, Feb. 19, 2009.
Kujovich, "Factor V Leiden thrombophilia", Genetics in Medicine, vol. 13, No. 1, Jan. 2011 , pp. 1-16.
Li et al., "Fast and accurate short read alignment with Burrows-Wheeler transform", Bioinformatics, May 18, 2009, vol. 25, No. 14, pp. 1754-1760.
Nelson et al., "The Population Reference Sample, POPRES: a resource for population, disease, and pharmacological genetics research", American Journal of Human Genetics, vol. 83, pp. 347-358, Sep. 12, 2008.
Paigen et al., "The recombinational anatomy of a mouse chromosome", PLoS Genetics, Jul. 2008, vol. 4, e1000119, 15 pgs., doi: 10.1371/journal.pgen.1000119.
Petkov et al., "Crossover interference underlies sex differences in recombination rates", Trends in Genetics, vol. 23, 539-542, Oct. 26, 2007.
Tajima et, "Estimation of Evolutionary Distance between Nucleotide Sequences", Molecular Biology and Evolution vol. 1, pp. 269-285 (1984).
Huber, "Robust Estimation of a Location Parameter", Ann. Math. Stat., 1964, vol. 35, pp. 73-101.
Joy et al., "High-Betweenness Proteins in the Yeast Protein Interaction Network", Journal of Biomedicine and Biotechnology, 2005, vol. 2, pp. 96-103.
Katzmarzyk et al., "Fitness, fatness and estimated coronary heart disease risk: the Heritage Family Study", Med Sci Sports Exerc, Apr. 2001, vol. 33, No. 4, pp. 585-90.
Kent et al., "The human genome browser at UCSC", Genome Research, vol. 12, 2002, pp. 996-1006.
Kimura, "The Neutral Theory of Molecular Evolution", Sci Am, 1979.
Kumar et al., "Phylomedicine: an evolutionary telescope to explore and diagnose the universe of disease mutations.", Trends Genet., 27(9):377-86, Sep 2011, Epub Jul. 20, 2011.
Kumar et al., "Predicting the effects of coding non-synonymous variants on protein function using the SIFT algorithm", Nature Protocols, 2009, vol. 4, No. 8, p. 1073-1082, Published online Jun. 25, 2009.
Lee et al., "A nucleocytoplasmic malate dehydrogenase regulates p53 transcriptional activity in response to metabolic stress", Cell Death and Differentiation, 2009, vol. 16, pp. 738-748.
Levy et al., "The Diploid Genome Sequence of an Individual Human", PLoS Biology, Oct. 2007, vol. 5, Issue 10, pp. 2113-2144.
Lo et al., "Developmental regulation and cellular distribution of human cytosolic malate dehydrogenase (MDH1)", J. Cell. Biochem., 2005, vol. 94, pp. 763-773.
Lohmueller et al., "Proportionally more deleterious genetic variation in European than in African populations", Nature, Letters, Feb. 21, 2008, vol. 451, pp. 994-997.
Manolio et al., "Finding the missing heritability of complex diseases", Nature, vol. 461, No. 7265, Oct. 8, 2009, pp. 747-753.
McClellan et al., "Genetic heterogeneity in human disease", Cell, vol. 141, Issue No. 2, pp. 210-217, Apr. 16, 2010.
Nicolaou et al., "Role of protein phosphatase-1 inhibitor-1 in cardiac physiology and pathophysiology", J. Mol. Cell Cardiol, Sep. 2009, vol. 47, No. 3, pp. 365-371.
Ounissi-Benkalha et al., "The molecular genetics of type 1 diabetes: new genes and emerging mechanisms", Trends, Mol Med. 14:268-275, 2008.
Park et al., "Estimation of effect size distribution from genome-wide association studies and implications for future discoveries", Nature Genetics, 42, 570-575, 2010.
Patel et al., "An Environment-Wide Association Study (EWAS) on Type 2 Diabetes Mellitus", PLoS ONE 5(5): e10746, May 20, 2010.
Poulsen et al., "Heritability of type II (non-insulin-dependent) diabetes mellitus and abnormal glucose tolerance—a population-based twin study", Diabetologia, 42(2):139-45, Feb. 1999.
Roberts, "Germlike gain-of-function mutations in SOS1 cause Noonan syndrome", Nature Genetics, 2007, vol. 39, pp. 70-74.
Sawyer et al., "Population Genetics of Polymorphism and Divergence", Genetics, 1992, vol. 132, pp. 1161-1176.
Schafer et al., "A Shrinkage Approach to Large-Scale Covariance Matrix Estimation and Implications for Functional Genomics", Statistical Application in Genetics and Molecular Biology, 2005, vol. 4, Issue, 1, Article 32 1175-1189.
Schafer et al., "An empirical Bayes approach to inferring large-scal gene association networks", Bioinformatics, 2005, vol. 21, No. 6, pp. 754-764.
Schaffter et al., "GeneNetWeaver: in silico benchmark generation and performance profiling of network inference methods", Bioinformatics, Jun. 22, 2011, vol. 27, No. 16, pp. 2263-2270.
Shabalin, "Matirx eQTL: ultra fast eQTL analysis via large matrix operations", Bioinformatics, 2012, vol. 28, No. 10, pp. 1353-1358.
Sing et al., "ROCR: visualizing classifier performance in R", Bioinformatics, 21:3940-3941, 2005.
Singh et al., "Abnormal Calcium Cycling and cardiac Arrhythmias Associated with the Homan SER96Ala Genetic Variant of Histidine-Rich Calcium-Binding Protein", Journal of the American Heart Association, 2013, vol. 2, 18 pgs.
Smoller et al., "Family, twin, and adoption studies of bipolar disorder", American Journal of Medical Genetics, vol. 123C, Issue No. 1, pp. 48-5815, Nov. 2003, First published Aug. 8, 2003.
Sofaer, "Crohn's disease: the genetic contribution", Gut, 34:869-871, 1993.
Tanaka et al., "Molecular cloning and mapping of a human dCNA for cytosolic malate dehydrogenase (MDHI)", Genomics, 1996, vol. 32, pp. 128130.
Thomas et al., "Coding single-nucleotide polymorphisms associated with complex vs. Mendelian disease: evolutionary evidence for differences in molecular effects", Proc Natl Acad Sci U S A., vol. 101, No. 43, pp. 15398-15403, Oct. 26, 2004.
Trapnell et al., "Differential gene and transcript expression analysis of RNA-seq experiments with TopHat and Cufflinks", Nature Protocols, 2012, vol. 7, No. 3, pp. 562-578.
Tusher et al., "Significance analysis of microarrays applied to the ionizing radiation response", PNAS, Apr. 24, 2001, vol. 98, No. 9, pp. 5116-5121.
Van Vliet-Ostaptchouk et al., "HHEX gene polymorphisms are associated with type 2 diabetes in the Dutch Breda cohort", European Journal of Human Genetics, 2008, vol. 16, pp. 652-656.
Wang et al., "The diploid Genome sequence of an Asian individual", Nature, Nov. 6, 2008, vol. 456, No. 7218, pp. 60-65.
Wei et al., "From Disease Association to Risk Assessment: An Optimistic View from Genome-Wide Association Studies on Type 1 Diabetes", PLoS Genet 5(10): e1000678, 2009.
Yang et al, "Overlapping community detection at scale: a nonnegative matrix factorization approach", In Proceedings of the sixth AMC international conference on Web search and data mining, 2013, pp. 587-596.
Grantham, "Amino acid difference formula to help explain protein evolution", Science, 1974, vol. 185, pp. 862-864.
Abi-Haidar et al., "Uncovering protein interaction in abstracts and text using a novel linear model and word proximity networks", Genome Biology 9(Suppl 2):S11, Sep. 1, 2008, 19 pgs.
Alex et al., "Automating curation using a natural language processing pipeline", Genome Biology 9(Suppl 2):S10, Sep. 1, 2008, 14 pgs.
Altman et al., "Text mining for biology—the way forward: opinions from leading scientists", Genome Biology 9(Suppl 2):S7, Sep. 1, 2008, 15 pgs.
Baumgartner Jr. et al., "Concept recognition for extracting protein interaction relations from biomedical text", Genome Biology 9(Suppl 2):S9, Sep. 1, 2008, 15 pgs.

(56) References Cited

OTHER PUBLICATIONS

Chatr-Aryamontri et al., "MINT and IntAct contribute to the Second BioCreative challenge: serving the text-mining community with high quality molecular interaction data", Genome Biology 9(Suppl 2):S5, Sep. 1, 2008, 8 pgs.

Hakenberg et al., "Gene mention normalization and interaction extraction with context models and sentence motifs", Genome Biology 9(Suppl 2):514, Sep. 1, 2008, 16 pgs.

Huang et al., "Mining physical protein-protein interactions from the literature", Genome Biology 9(Suppl 2):S12, Sep. 1, 2008, 13 pgs.

Krallinger et al., "Linking genes to literature: text mining, information extraction, and retrieval applications for biology", Genome Biology, 9 (Suppl 2): S8, Sep. 1, 2008.

Leitner et al., "Introducing meta-services for biomedical information extraction", Genome Biology 9(Suppl 2):56, Sep. 1, 2008, 11 pgs.

Morgan et al., "Overview of BioCreative II gene normalization", Genome Biology 9(Suppl 2):S3, Sep. 1, 2008, 19 pgs.

Rinaldi et al., "OntoGene in BioCreative II", Genome Biology 9(Suppl 2):513, Sep. 1, 2008, 11 pgs.

Smith et al., "Overview of BioCreative II gene mention recognition", Genome Biology, 9 (Suppl 2):S2, Sep. 1, 2008, 19 pgs.

Cytoscape 2.6.2, Cytoscape Consortium, May 12, 2009, Retrieved from: https://web.archive.org/web/20090512221703/http://cytoscape.org/, 7 pgs.

Adzhubei et al., "A method and server for predicting damaging missense mutations", Nature Methods, vol. 7, No. 4, Apr. 2010, pp. 248-249.

Akashi et al., "Translational selection and molecular evolution", Curr. Opin. Genet. Dev. 1998; 8: 688-693.

Alexiou et al., "Lost in translation: an assessment and perspective for computational microRNA target identification", Bioinformatics. 2009; 25:3049-3055.

Barabasi et al., "Emergence of Scaling in Random Networks", Science. 1999, vol. 286, pp. 509-512.

Barbacioru et al., "Effect of various normalization methods on Applied Biosystems expression array system data", BMC Bioinformatics 2006, 7:533, 14 pgs.

Baudat et al., "PRDM9 is a major determinant of meiotic recombination hotspots in humans and mice", Science 327, 836-840, May 7, 2010.

Bell et al., "Carrier Testing for Severe Childhood Recessive Diseases by Next-Generation Sequencing", Science Translational Medicine, vol. 3: 65ra4, Jan. 12, 2011, 26 pgs.

Bloss et al., "Effect of Direct-to-Consumer Genomewide Profiling to Assess Disease Risk", The New England Journal of Medicine, vol. 364, Feb. 10, 2011, pp. 524-534.

Chamary et al., "Hearing silence: non-neutral evolution at synonymous sites in mammals", Nature Reviews Genetics, Feb. 2006, vol. 7, pp. 98-108.

Chen et al., "The reference human genome demonstrates high risk of type 1 diabetes and other disorders", Pac Symp Biocomput, 231-242, 2011.

Chen et al., "Variations in DNA elucidate molecular networks that cause disease", Nature, 2008; 452:429-435; doi:10.1038/nature06757.

Chien, "Stress pathways and heart failure", Cell. Sep. 3, 1999; 98: 555-558.

Coffer et al., "Forkhead-box transcription factors and their role in the immune system", Nat Rev Immunol. 2004; 4:889-899.

Cooper et al., "Distribution and intensity of constraint in mammalian genomic sequence", Genome Research, vol. 15, No. 7, Jun. 2005, pp. 901-913.

Cooper et al., "Single-nucleotide evolutionary constraint scores highlight disease-causing mutations", Nature Methods, vol. 7, No. 4, Apr. 2010, pp. 250-251.

Dennis et al., "David: Database for Annotation, Visualization, and Integrated Discovery", Genome Biol. 2003; 4:P3, 11 pgs.

Gaur et al., "The heart of metamorphosing Mexican axolotl but not that of the cardiac mutant is associated with the upregulation of Hox A5", Biochem Biophys Res Commun. 1998; 245:746-751.

Hamosh et al., "Online Mendelian Inheritance in Man (OMIM) a knowledgebase of human genes and genetic disorders", Nucleic Acids Research, 2002, vol. 30, pp. 52-55.

Hannenhalli et al., "Transcriptional genomics associates FOX transcription factors with human heart failure", Circulation. 2006; 114:1269-1276.

Hansson et al., "A switch in metabolism precedes increased mitochondrial biogenesis in respiratory chain-deficient mouse hearts", Proc Natl Acad Sci U S A. 2004; 101:3136-3141.

Hidaka et al., "Differentiation of Pharyngeal Endoderm and Derivatives from Mouse Embryonic Stem Cells", Stem Cells Dev. 2010; 19:1735-1743.

Hindorff et al., "Potential etiologic and functional implications of genome-wide association loci for human diseases and traits", Proc Natl Acad Sci USA, Jun. 9, 2009. 106(23): pp. 9362-9367, PMCID: 2687147.

Hofacker, "Vienna RNA secondary structure server", Nuc. Acid Res., Apr. 5, 2003, vol. 31, No. 13, pp. 3429-3431.

Hoppe et al., "Marburg I polymorphism of factor VII-activating protease is associated with idiopathic venous thromboembolism", Blood 105, 1549-1551, Feb. 15, 2005.

Horvath et al., "Geometric interpretation of gene coexpression network analysis", PLoS Comput Biol. 2008, vol. 4, Issue 8; 4:e1000117, 27 pgs.

Hoshijima et al., "Mixed signals in heart failure: cancer rules", J Clin Invest. 2002; vol. 109, No. 7, pp. 849-855.

Hu et al., "VisANT 3.5: multiscale network visualization, analysis and inference based on the gene ontology", Nucleic Acids Res. 2009; vol. 37, Web Server Issue, pp. W115-W121.

Huang et al., "Systematic and integrative analysis of large gene lists using DAVID bioinformatics resources", Nat Protoc. 2009, Published online Dec. 18, 2008, vol. 4, No. 1, pp. 44-57.

Ikem Ura, "Codon usage and tRNA content in unicellular and multicellular organisms", Molecular Biology and Evolution, vol. 2, No. 1, 1985, pp. 13-34.

Jeong et al., "Lethality and centrality in protein networks", Nature. 2001; 411:41-42.

Jeong et al., "The large-scale organization of metabolic networks", Nature, Oct. 5, 2000; vol. 407, pp. 651-654.

Jhund et al., "Long-term trends in first hospitalization for heart failure and subsequent survival between 1986 and 2003: a population study of 5.1 million people", Circulation. 2009; 119:515-523.

Johnson et al., "Snap: a web-based tool for identification and annotation of proxy SNPs using HapMap", Bioinformatics, Oct. 30, 2008, vol. 24, No. 24, pp. 2938-2939.

Kim et al., "Hoxa-5 in mouse developing lung: cell-specific expression and retinoic acid regulation", Am J Physiol Lung Cell Mol Physiol. 2000; vol. 279, pp. L863-L871.

Kimchi-Sarfaty et al., "A "Silent" Polymorphism in the MDR1 Gene Changes Substrate Specificity", Science, Jan. 26, 2007, vol. 315, No. 5811, pp. 525-528.

Klein et al., "Estimation of the Warfarin Dose with Clinical and Pharmacogenetic Data", New England Journal of Medicine, vol. 360, 753-764, Feb. 19, 2009.

Kong et al., "Fine-scale recombination rate differences between sexes, populations and individuals", Nature, vol. 467, No. 7319, pp. 1099-1103, Oct. 28, 2010.

Kong et al., "Parental origin of sequence variants associated with complex diseases", Nature, vol. 462, No. 7275, Dec. 17, 2009, pp. 868-874.

Kong et al., "Sequence variants in the RNF212 gene associate with genome-wide recombination rate", Science 319, 1398-1401, Mar. 7, 2008.

Koster et al., "Venous thrombosis due to poor anticoagulant response to activated protein C: Leiden Thrombophilia Study", Lancet 342, 1503-1506, Dec. 18/25, 1993.

Kumar et al., "MEGA3: Integrated software for Molecular Evolutionary Genetics Analysis and sequence alignment", Briefings in Bioinformatics vol. 5, pp. 150-163 (2004).

(56) References Cited

OTHER PUBLICATIONS

Kumar et al., "Predicting the effects of coding non-synonymous variants on protein function using the SIFT algorithm", Nature Protocols, 2009 vol. 4, pp. 1073-1082.
Langfelder et al., "Defining clusters from a hierarchical cluster tree: the Dynamic Tree Cut package for R", Bioinformatics. 2008, vol. 24. No. 5, pp. 719-720.
Langfelder et al., "Eigengene networks for studying the relationships between co-expression modules", BMC Syst Biol. 2007, pp. 1-54; doi:10.1186/1752-0509.
Levy et al., "Identification of transcription factor binding sites in the human genome sequence", Mammalian Genome, 2002, vol. 13, pp. 510-514; DOI:10.1007/s003350010117.
Lyn et al., "Gene expression profile in mouse myocardium after ischemia", Physiol Genomics. 2000; vol. 2, pp. 93-100.
Macaya et al., "A synonymous mutation in TCOF1 causes Treacher Collins syndrome due to mis-splicing of a constitutive exon", Am J Med Genet Part a, Feb. 24, 2009, vol. 149A, pp. 1624-1627.
Margaglione et al., "The methylenetetrahydrofolate reductase TT677 genotype is associated with venous thrombosis independently of the coexistence of the FV Leiden and the prothrombin A20210 mutation", Thromb Haemost 79, 907-911, Jan. 5, 1998.
Matkovich et al., "Reciprocal regulation of myocardial microRNAs and messenger RNA in human cardiomyopathy and reversal of the micro RNA signature by biomechanical support", Circulation. 2009; 119:1263-1271.
Supplementary materials and method for "Phased Whole-Genome Genetic Risk in a Family Quartet Using a Major Allele Reference Sequence", PLOS Genetics, Published Sep. 15, 2011, Retrieved from: https://doi.org/10.1371/journal.pgen.1002280.s017.
"A Catalog of Published Genome-Wide Association Studies", Retrieved from: https://web.archive.org/web/20110727063625/http://www.genome.gov/gwastudies/, Jul. 27, 2011, Printed on Jun. 19, 2017, 3 pages.
Chanock et al., "Replicating genotype-phenotype associations", NCI-NHGRI Working Group on Replication in Association Studies, Nature, vol. 447, Jun. 7, 2007, 6 pgs.
The International HapMap 3 Consortium, "Integrating common and rare genetic variation in diverse human populations", Nature, 467(7311), Sep. 2, 2010, pp. 52-58; doi:10.1038/nature09298.
Ahn et al., "Link Communities Reveal Multiscale Complexity in Networks", Nature, 466, Aug. 2010, pp. 761-764.
Arvanitis et al., "The Ser96Ala variant in histidine-rich calcium-binding protein is associated with life-threatening ventricular arrhythmias in idiopathic dilated cardiomyopathy", European Heart Journal, 2008, vol. 29, pp. 2514-2525.
Aten et al., "Using genetic markers to orient the edged in quantitative trait networks: The NEO software", BMV Systems Biology, Apr. 15, 2008, vol. 2, No. 34, 21 pgs.
Berrebi-Bertrand et al., "Biophysical interaction between phospholamban and protein phosphatase 1 regulatory subunit GM", FEBS Letters, 1998, vol. 439, pp. 224-230.
Blekhman et al., "Natural selection on genes that underlie human disease susceptibility", Curr Biol, 18(2):883-889, Jun. 24, 2008.
Bodmer et al., "Common and rare variants in multifactorial susceptibility to common diseases", Nat Genet., 40(6): 695-701, Jun. 2008.
Boyle et al., "Annotation of functional variation in personal genomes usign RegulomeDB", Genome research 22:1790-1797, 2012.
Cai et al., "Similarly strong purifying selection acts on human disease genes of all evolutionary ages", Genome Biol Evol., 1:131-44, May 27, 2009.
Chen et al., "Non-synonymous and Synonymous Coding SNPs Show Similar Likelihood and Effect Size of Human Disease Association", PLoS One, vol. 5, Issue 10, Oct. 22, 2010, e13574-1-e13574-6.
Cooper et al., "A genome-wide scan for common genetic variants with a large influence on warfarin maintenance dose", Blood, Aug. 15, 2008, vol. 112, No. 4, pp. 1022-1027.
Cordero et al., "A Community Overlap Strategy Reveals Central Genes and Networks in Heart Failure", bioRxiv preprint first posted online Jan. 28, 2016; doi: http://dx.doi.org/10.1101/038174, 52 pgs.
Danaher et al, "The joint graphical lasso for inverse covariance estimation across multiple classes", J. R. Stat. Soc. Ser. B (Statistical Methodol., 2014, vol. 76, pp. 373-397; arXiv:1111.0324, Jul. 11, 2012.
Dewey et al., "Gene Coexpression Network Topology of Cardiac Development, Hypertrophy and Failure", Circ. Cardiovasc. Genet., Feb. 2011, 4(1), 16 pgs.
Dickson et al., "Rare Variants Create Synthetic Genome-Wide Associations", PLOS Biology, 8(1): e1000294, Jan. 26, 2010, 12 pgs.
Dobin et al., "STAR: ultrafast universal RNS-seq aligner", Bioinformatics, 2013, vol. 29, No. 1, pp. 15-21.
Eble et al., "Contractile activity is required for sarcomeric assembly in phenylephrine-induced cardia myocyte hypertrophy", Am. J. Physiol., 1998, vol. 274, pp. C1226-C1237.
Eichler et al., "Missing heritability and strategies for finding the underlying causes of complex disease", Nat Rev Genet., Author manuscript; Final version published: Nat. Rev. Genet. 11(6): 446-450, Jun. 2010.
Faust, "Centrality in affiliation networks", Social Networks, 1997, vol. 19, pp. 157-191.
Feero et al., "Genomewide association studies and assessment of the risk of disease", The New England Journal of Medicine, 2010, vol. 363, pp. 166-176.
Friedman et al., "Sparse inverse covariance estimation with the graphical lasso", Biostatistics, Dec. 12, 2007, vol. 9, pp. 432-441.
Green et al., "Charting a course for genomic medicine from base pairs to bedside", Nature, vol. 470, Feb. 10, 2011, pp. 204-213.
Han et al., "A long noncoding RNA protects the heart from pathological hypertrophy", Nature, Oct. 2, 2014, vol. 514, No. 7520, pp. 102-106.
Hansen et al., "Generating Genome-Scale Candidate Gene Lists for Pharmacogenomics", Clin. Pharmacol. Ther., Aug. 2009, vol. 86, No. 2, pp. 183-189.
Harney et al., "Fine mapping of the MHC Class III region demonstrates association of AIF1 and rheumatoid arthritis", Rheumatology 2008, 47:1761-1767, Advance publication Oct. 3, 2008, 7 pgs.
Hedges et al., "TimeTree: a public knowledge-base of divergence times among organisms", Bioinformatics, Applications Note, 2006, vol. 22, No. 23, pp. 2971-2972.
Hernandez et al., "Classic Selective Sweeps Were Rare in Recent Human Evolution", Science, Apr. 8, 2011, vol. 331, pp. 920-924.
"Genome-wide association study of 14,000 cases of seven common diseases and 3,000 shared controls", The Wellcome Trust Case Control Consortium, Nature, vol. 447, pp. 661-678 Jun. 7, 2007.
Agarwal et al., "Genetics of human hypertension", Trends Endocrinology & Metabolism, vol. 16, Issue No. 3, pp. 127-133, Apr. 2005.
Barreiro et al., "Natural selection has driven population differentiation in modern humans", Nat. Genet., 40(3): 340-5, Mar. 2008.
Frey et al., "Mechanisms of disease: hypertrophic cardiomyopathy", Nat. Rev. Cardiol., 2012, vol. 9, pp. 91-100.
Goldstein, "Common Genetic Variation and Human Traits", The New England Journal of Medicine, Apr. 23, 2009, vol. 360, pp. 1696-1698.
Brennan et al., "Amechanism for the HLA-A*01—associated risk for EBV Hodgkin lymphoma and infectious mononucleosis", Blood, vol. 112, No. 6, Sep. 15, 2008, pp. 2589-2590.
Dobyns et al., "Management of Thumb Duplication", Clin Orthop 1985; 195: 26-44.
Hirschman et al., "The BioCreative II—Critical Assessment for Information Extraction in Biology Challenge", vol. 9, Suppl. 2, Genome Biology, Madrid, Spain, Apr. 23-25, 2007.
Johnson et al., "An Open Access Database of Genome-wide Association Results BMC", Medical Genetics, Jan. 22, 2009, vol. 10, No. 6, 17 pgs., doi: 10.1186/1471-2350-10-6.
Kohane et al., "The incidentalome: a threat to genomic medicine", The Journal of the American Medical Association, vol. 296, No. 2, Jul. 11, 2006, pp. 212-215.

(56) References Cited

OTHER PUBLICATIONS

Kong et al., "A high-resolution recombination map of the human genome", Nature Genetics, vol. 31, 241-247, Jul. 2002.
Krallinger et al., "Evaluation of text-mining systems for biology: overview of the Second BioCreative community challenge", Genome Biology vol. 9, Article 51, Sep. 1, 2008.
Krallinger et al., "Overview of the protein-protein interaction annotation extraction task of BioCreative II", Genome Biology vol. 9, Article S4, Sep. 1, 2008.
Kuwahara et al., "NRSF regulates the fetal cardiac gene program and maintains normal cardiac structure and function", Embo Journal, 2003; vol. 22, No. 23, pp. 6310-6321.
McKenna et al., "The Genome Analysis Toolkit: A MapReduce framework for analyzing next-generation DNA sequencing data", Genome Research, vol. 20, Jul. 12, 2010, pp. 1297-1303.
Myers et al., "Drive against hotspot motifs in primates implicates the PRDM9 gene in meiotic recombination", Science 327, 876-879, Jan. 8, 2010.
Nakamura et al., "The mediator complex subunit 1 enhances transcription of genes needed for adrenal androgen production", Endocrinology, 2009; 150:4145-4153.
Ng et al., "Predicting Deleterious Amino Acid Substitutions", Genome Res., Mar. 13, 2001, vol. 11, No. 5, pp. 863-874.
Ng et al., "SIFT: Predicting amino acid changes that affect protein function", Nucleic Acids Research, vol. 31, No. 13, Feb. 28, 2003, pp. 3812-3814.
Nowell et al., "Pharmacogenetics of human cytosolic sulfotransferases", Oncogene. 2006; 25:1673-1678.
Oldham et al., "Conservation and evolution of gene coexpression networks in human and chimpanzee brains", Proc Natl Acad Sci U S A. 2006; 103:17973-17978.
Ormond et al., "Challenges in the clinical application of whole-genome sequencing", Lancet, vol. 375, May 15, 2010, published online Apr. 30, 2010, pp. 1749-1751.
Parvanov et al., "Prdm9 Controls Activation of Mammalian Recombination Hotspots", Science 327, 835, Feb. 12, 2010, Published online: Dec. 31, 2009.
Pruitt et al., "NCBI reference sequences (RefSeq): a curated non-redundant sequence database of genomes, transcripts and proteins", Nucleic Acids Research, vol. 35, 2007, published online Nov. 27, 2006, pp. D61-65, doi:10.1093/nar/gkl842.
Pushkarev et al., "Single-molecule sequencing of an individual human genome", Nature Biotech., Sep. 2009, vol. 27, no. 9, pp. 847-850, doi: 10.1 038/nbt.1561.
Rajabi et al., "Return to the fetal gene program protects the stressed heart: a strong hypothesis", Heart Fail Rev. 2007; 12:331-343.
Rasmussen et al., "Ancient human genome sequence of an extinct Palaeo-Eskimo", Nature, Feb. 11, 2010, vol. 463, pp. 757-762.
Ridker et al., "Interrelation of Hyperhomocyst(e)inemia, Factor V Leiden, and Risk of Future Venous Thromboembolism", Circulation 95, 1777-1782, 1997.
Ridker et al., "Mutation in the gene coding for coagulation factor V and the risk of myocardial infarction, stroke, and venous thrombosis in apparently healthy men", N Eng I J Med 332, 912-917, Apr. 6, 1995.
Ripatti et al., "A multilocus genetic risk score for coronary heart disease: case-control and prospective cohort analyses", Lancet, vol. 376, No. 9750, Oct. 23, 2010, pp. 1393-1400.
Rivas et al., "Secondary structure alone is generally not statistically significant for the detection of noncoding RNAs", Bioinformatics, vol. 16, No. 7, 2000, pp. 583-605.
Roach et al., "Analysis of genetic inheritance in a family quartet by whole-genome sequencing", Science 328, 636-639, Feb. 16, 2010.
Roemisch et al., "The frequent Marburg I polymorphism impairs the prourokinase activating potency of the factor VII activating protease (FSAP)", Blood Coagulation and Fibrinolysis 13, 433-441, Apr. 3, 2002.
Rogers et al., "Radial styloid impingement after triscaphe arthrodesis", J. Hand Surg., Mar. 1989, vol. 14A, No. 2, Part 1, pp. 297-301.

Samani et al., "The personal genome—the future of personalised medicine?", Lancet, vol. 375, May 1, 2010, pp. 1497-1498.
Schadt, "Molecular networks as sensors and drivers of common human diseases", Nature. 2009; 461:218-223.
Scott et al., "Clinical Pharmacogenetics Implementation Consortium Guidelines for Cytochrome P450-2C19 (CYP2C19) Genotype and Clopidogrel Therapy", Clinical Pharmacology and Therapeutics, vol. 90, No. 2, Aug. 2011, pp. 328-332.
Sedding et al., "The G534E polymorphism of the gene encoding the factor VII-activating protease is associated with cardiovascular risk due to increased neointima formation", Exp Med 203, 2801-2807, Dec. 25, 2006.
Shiina et al., "An update of the HLA genomic region, locus information and disease associations: 2004", Tissue Antigens, vol. 64, No. 6, Aug. 8, 2004, pp. 631-649.
Smith et al., "Mutations in ATP6NIB, encoding a new kidney vacuolar proton pump 116-kD subunit, cause recessive distal renal tubular acidosis with preserved hearing", Nature Genetics, vol. 26, pp. 71-75, Sep. 2000.
Smith et al., "The Causes of Synonymous Rate Variation in the Rodent Genome: Can Substitution Rates Be Used to Estimate the Sex Bias in Mutation Rate?", Genetics, Feb. 16, 1999, vol. 152, pp. 661-673.
Storey et al., "Statistical methods for identifying differentially expressed genes in DNA microarrays", Methods Mol Biol. 2003; 224:149-157.
Thattaliyath et al., "HAND 1 and HAND2 are expressed in the adult-rodent heart and are modulated during cardiac hypertrophy", Biochem Biophys Res Commun. 2002; 297:870-875.
Thum et al., "MicroRNAs in the human heart: a clue to fetal gene reprogramming in heart failure", Circulation, 2007; 116:258-267.
Tjon et al., "Celiac disease: how complicated can it get?", Immunogenetics, vol. 62, No. 10, Jul. 27, 2010, pp. 641-651.
Trivedi et al., "Hdac2 regulates the cardiac hypertrophic response by modulating Gsk3 beta activity", Nat Med. 2007; 13:324-331.
Van Belle et al., "Type 1 Diabetes: Etiology, Immunology, and Therapeutic Strategies", Physiological Reviews, vol. 91, No. 1, Jan. 2011, pp. 79-118.
Van Rooij et al., "A signature pattern of stress-responsive microRNAs that can evoke cardiac hypertrophy and heart failure", Proc Natl Acad Sci USA. 2006; 103:18255-18260.
Vanderheyden et al., "Myocardial Gene Expression in Heart Failure Patients Treated with Cardiac Resynchronization Therapy Responders Versus Nonresponders", J Am Coll Cardiol. 2008; 51:129-136.
Watterson, "On the Number of Segregating Sites in Genetical Models Without Recombination", Theoretical Population Biology, vol. 7, 1975, pp. 256-276.
Wingender et al., E., "TRANSFAC: a database on transcription factors and their DNA binding sites", Nucleic Acids Res, 1996; 24:238-241.
Yang et al., "Validation of candidate causal genes for obesity that affect shared metabolic pathways and networks", Nat Genet. 2009; 41:415-423.
Yeo et al., "Maximum Entropy Modeling of Short Sequence Motifs with Applications to RNA Splicing Signals", Journal of Computational Biology, Feb. 2004, vol. 11, No. 2-3, pp. 377-394.
Yip et al., "Gene network interconnectedness and the generalized topological overlap measure", BMC Bioinformatics. 2007, vol. 8, No. 22, 14 pgs.
Yue et al., "Post-infarction Heart Failure in the Rat is Associated with Distinct Alterations in Cardiac Myocyte Molecular Phenotype", J Mol Cell Cardiol. 1998; 30:1615-1630.
Zhang et al., "A General Framework for Weighted Gene Co-Expression Network Analysis", Stat Appl Genet Mol Biol. 2005; 4:Article17.
Zhang et al., "Generic Algorithm to Predict the Speed of Translational Elongation: Implications for Protein Biogenesis", PLoS ONE, Apr. 3, 2009, vol. 4, Issue 4, No. e5036, pp. 1-9, doi: 1 0.1371/joumal.pone.0005036.
Mao et al., "Arabidopsis gene co-expression network and its functional modules", BMC Bioinformatics, Oct. 2009, 10:346, pp. 1-24.

(56) References Cited

OTHER PUBLICATIONS

Ruan et al., "A general co-expression network-based approach to gene expression analysis: comparison and applications", BMC Systems Biology, 2010, 4:8, pp. 1-21.

* cited by examiner

Table 1

| Algorithm actions | | |
|---|---|---|
| (i) Expand seed | (ii) End expansion | (iii) Interrupt |
| Expanded seed is subject | Expanded seed is object | All others |
| Dependency types | nn (noun modifier) | dobj (direct object) |
| | | iobj (indirect object) |
| | prep_{for,in,into,of,on,to} (preposition) | xcomp (open clausal component) |
| | nsubj (nominal subject) | |
| | nsubjpass (passive nominal subject) | prep_{at,as,by,for,in,into,on,than,with,within} (preposition) |
| | xsubj (controlling subject) | |

Fig. 10

Table 2

| Relationship types | Entities modified by Genes | Drugs | Phenotypes |
|---|---|---|---|
| 2538 associate | 1237 gene | 267 metabolism | 304 cell |
| 1017 increase | 1000 inhibitor | 229 activity | 114 line |
| 985 inhibit | 935 polymorphism | 226 administration | 101 patient |
| 825 induce | 775 expression | 213 treatment | 71 risk |
| 763 metabolize | 773 activity | 207 effect | 35 tissue |
| 666 involve | 689 mutation | 205 inhibitor | 34 specimen |
| 643 reduce | 685 genotype | 146 dose | 33 case |
| 547 catalyze | 393 inhibition | 137 concentration | 27 treatment |
| 515 cause | 329 level | 104 level | 26 rate |
| 509 affect | 245 gene_mutation | 103 substrate | 26 effect |
| 490 decrease | 232 gene_polymorphi | 90 clearance | 26 breast = cancer |
| 433 show | 227 allele | 88 antagonist | 22 incidence |
| 428 express | 162 variant | 84 channel | 21 factor |
| 392 relate | 156 enzyme | 75 inhibition | 21 resistance |
| 392 use | 138 mrna | 73 responsible | 20 sample |
| 387 correlate | 125 protein | 72 hydroxylation | 18 model |
| 385 influence | 83 channel | 70 enzyme | 16 exposure |
| 355 determine | 81 isoform | 67 oxidation | 15 type |
| 354 contribute | 78 effect | 65 gene | 15 development |
| 319 factor | 77 isozyme | 63 formation | 15 group |
| 318 mediate | 76 cell | 62 blocker | 14% |
| 317 had | 73 deficiency | 60 metabolite | 14 activity |
| 301 found | 71 overexpression | 57 dependent | 14 mellitus |
| 299 measure | 67 substrate | 52 exposure | 13 gene |
| 287 investigate | 67 induction | 46 ratio | 13 cause |
| 284 result | 63 gene_expression | 45 consumption | 13 presence |
| 281 studied | 59 c677t | 44 due | 13 all |
| 280 detect | 58 inhibitor_use | 43 drug | 13 level |
| 274 association | 57 gene_allele | 40 response | 12 severity |
| 274 have | 55 content | 38 bioavailability | 12 study |

Fig. 11

Table 3

| Percentage of covered raw relationships | Relationship types (n = 1921) (%) | Entities modified by | | |
|---|---|---|---|---|
| | | Genes (n = 1210) (%) | Drugs (n = 1243) (%) | Phenotypes (n = 445) (%) |
| By 100 most frequent relationship types or entities | 68 | 77 | 58 | 71 |
| By 200 most frequent relationship types or entities | 80 | 85 | 71 | 84 |

Fig. 12

Table 4

| Roles | Concepts modified by | | |
|---|---|---|---|
| | Drug | Gene | Phenotype |
| 2981 associated_with | 6075 (1083) Drug | 8040 (285) Gene | 3854 (930) Disease |
| 1580 demonstrates | 1063 (558) DrugTreatment | 2082 (210) Variant | 604 (354) PhenotypeRisk |
| 1460 increases | 606 (344) DrugDose | 2702 (187) Expression | 211 (163) DiseaseExacerbation |
| 1428 reduces | 302 (160) DrugEffect | 826 (134) GenomicVariation | 171 (183) DiseaseSeverity |
| 1420 studies | 263 (195) DrugMetabolism | 644 (64) Enzyme | 117 (95) Symptom |
| 986 inhibits | 199 (135) DrugActivity | 520 (185) GeneProductFunction | 99 (77) DiseaseCause |
| 924 influences | 130 (107) DrugElimination | 192 (103) GeneProductSynthesis | 57 (38) DiseaseSensitivity |
| 894 causes | 137 (90) DrugTransformation | 592 (103) Repression | 49 (53) PhenotypeMechanism |
| 841 includes | 101 (61) Hydroxylation | 317 (79) Overexpression | 49 (36) Phenotype |
| 707 metabolizes | 93 (75) DrugAnalysis | 285 (81) GeneProductActivity | 44 (38) DiseaseEffect |
| 698 uses | 88 (81) DrugPharmacokinetics | 169 (67) Protein | 29 (33) DiseaseRelief |
| 655 induces | 87 (72) DrugMetabolite | 128 (81) GeneAnalysis | 27 (35) PhenotypeAnalysis |
| 488 produces | 80 (62) DrugInhibitor | 88 (75) GenomicRegion | 25 (24) DiseaseDuration |
| 464 affects | 67 (62) DrugDoseVariation | 73 (44) GeneProduct | 9 (10) DiseaseSurvival |
| 449 determines | 59 (59) DrugAnalog | 57 (50) GeneProductActivityChange | 5 (13) DiseaseAbsence |

Fig. 13

METHOD AND SYSTEM FOR EXTRACTION AND NORMALIZATION OF RELATIONSHIPS VIA ONTOLOGY INDUCTION

CROSS-REFERENCE TO RELATED APPLICATIONS

This application claims priority to U.S. Provisional Application No. 61/491,103 filed May 27, 2011, which is hereby incorporated by reference in its entirety for all purposes.

STATEMENT OF GOVERNMENT SPONSORED SUPPORT

This invention was made with Government support under contracts GM061374 and HG004028 awarded by the National Institutes of Health. The Government has certain rights in this invention.

FIELD OF THE INVENTION

The present invention generally relates to the field of biomedical informatics. More particularly, the present invention relates to methods for natural language processing of bioinformatics.

BACKGROUND OF THE INVENTION

Much biological knowledge exists in published scientific text. In order to support the creation of databases and to enable the discovery of new relationships, there is great interest in extracting relationships automatically. Several efforts use manually created rules to define patterns of relationships between entities. These approaches are efficient when used in domains that are of limited scope, such as protein-protein interactions or protein transport. However, the complexity and diversity of the semantics used to describe relationships in broad or evolving domains, such as pharmacogenomics (PGx), are harder to capture. No general set of rules exists for extracting the relationships relevant to such fields, and creating/maintaining them manually would be tedious and time consuming.

Syntactic sentence parsers can identify the subject, object, and type of relationships using grammatical rules. General statistical parsing techniques have recently emerged, and there are several general-purpose parsers that yield reasonable results when applied to scientific text. These parsers depend on the need for good domain-specific lexicons of key entities, since named-entity recognition for particular fields in science can be difficult.

Current methods of text mining to extract relationships have at least the following limitations:
- Modified entities are not recognized;
- Extracted relationships are restricted to a set of pre-defined relationships; and
- Extracted entities and relationships are not normalized in a manner that maps concepts into a common framework.

The lack of recognizing of modified entities is a problem since the true relationship described in the sentence is often that between specific entities specified by the modifications of the seed terms. The relationships between the two entities can be diverse. Moreover, pre-specification of allowable relationships is time-consuming, non-robust and infeasible given the varied types of relationships used in natural language textual documents. The lack of normalization is problematic because there is no way to collapse heterogeneous ways of stating the same relationship to aggregate identical facts stated differently in the free-form literature.

Background for the teachings of the present invention include efforts in building the Pharmacogenomic Knowledge Base, PharmGKB (http://www.phar-mgkb.org/) (Klein T, Chang J, Cho M, Easton K, Fergerson R, Hewett M, et al. Integrating genotype and phenotype information: an overview of the PharmGKB project. Pharmacogenomics J 2001; 1(3):167-70; these and all other references cited herein are incorporated by reference for all purposes). An aim of PharmGKB is to catalog all knowledge of how human genetic variation impacts drug-response phenotypes, and is a curated database that summarizes published gene-drug-phenotype relationships.

The rapidly increasing size of the pharmacogenomic literature threatens to overwhelm the PharmGKB curators. Automatic approaches using NLP techniques are promising. Methods based on co-occurrence assume that entities occurring together in a sentence are related, but the semantics of the relationships are not typically captured. Nevertheless, these approaches efficiently identify potential relationships that can subsequently be evaluated. For example, the Pharmspresso system uses co-occurrence to group frequently co-mentioned genes, genomic variations, drugs, and diseases (Garten Y, Altman R B. Pharmspresso: a text mining tool for extraction of pharmacogenomic concepts and relationships from full text. BMC Bioinformatics 2009; 10 (S-2)). These groups are then used to assist curation. Li et al. used the co-occurrence of drug and disease names in MEDLINE abstracts to derive drug-disease relations and to build a disease-specific drug-protein network (Li J, Zhu X, Chen J Y. Building disease-specific drug-protein connectivity maps from molecular interaction networks and pubmed abstracts. PLoS Comput Biol 2009; 5(7):e1000450+). Blaschke et al. and Rosario et al. expanded this co-occurrence approach to extract more complete relations by searching for "tri-co-occurrence" (Blaschke C, Andrade M A, Ouzounis C, Valencia A. Automatic extraction of biological information from scientific text: protein-protein interactions. In: ISMB; 1999. p. 60-7; Rosario B, Hearst M A. Classifying semantic relations in bioscience texts. In: ACL; 2004. p. 430-7). Tri-co-occurrence refers to the co-occurrence of two named entities and one type of relationship in a unique piece of text. Statistical analysis of co-occurrence can help derive semantic similarities between entities (Cohen T, Widdows D. Empirical distributional semantics: methods and biomedical applications. J Biomed Inform 2009; 42(2):390-405).

In contrast to co-occurrence, syntactic parsing can explicitly identify relationships between two entities in text (Wermter J, Hahn U. You can't beat frequency (unless you use linguistic knowledge)—a qualitative evaluation of association measures for collocation and term extraction. In: ACL; 2006). Hand-coded parsing rules can extract protein-protein interactions and protein transport relationships (Hirschman L, Krallinger M, Wilbur J, Valencia A, editors. The biocreative II—critical assessment for information extraction in biology challenge, vol. 9, Genome Biology; 2008; (Tsujii J, editor. In: Proceedings of the BioNLP 2009 workshop companion volume for shared task; 2009). Fundel et al. defined three general patterns of relations (specifying the semantic type of subjects and objects, and using a lexicon of association words) to identify protein-protein interactions (Fundel K, Kuffner R, Zimmer R. Relex—relation extraction using dependency parse trees. Bioinformatics 2007; 23(3):365-71). For example their pattern "effector-relation-effectee" enables the capture of relationships of the form "protein A activates protein B". The OpenDMAP system also uses patterns to identify protein interaction and transport (Hunter L, Lu Z, Firby J, Baumgartner Jr W A, Johnson H L, Ogren P V, Cohen K B. OpenDMAP: an open-source, ontology-driven concept analysis engine, with applications to capturing knowledge regarding protein transport, protein interactions and cell-type-specific gene expression. BMC Bioinformatics 9(78)). Ahlers et al. used vocabularies and semantic types of the UMLS (Unified Medical Language System) to specify patterns to extract gene-disease and drug-disease relationships (Ahlers C B, Fiszman M, Demner-Fushman D, Lang F-M, Rindflesch T C. Extracting semantic predications from MEDLINE citations for pharmacogenomics. In: Pacific Symposium on Biocomputing; 2007, pp. 209-220). Several groups have used extracted relationships to create networks, including molecular interaction networks (Friedman C, Kra P, Yu H, Krauthammer M, Rzhetsky A. Genies: a natural-language processing system for the extraction of molecular pathways from journal articles. In: ISMB (supplement of bioinformatics); 2001. p. 74-82), gene-disease networks (Rindflesch T C, Libbus B, Hristovski D, Aronson A R, Kilicoglu H. Semantic relations asserting the etiology of genetic diseases. In: AMIA Annu Symp Proc 2003; 2003. p. 554-8), regulatory gene expression networks (Saric J, Jensen L J, Ouzounova R, Rojas I, Bork P. Extraction of regulatory gene/protein networks from MEDLINE. Bioinformatics 2006; 22(6):645-50), and gene-drug-disease networks (Tari L, Hakenberg J, Gonzalez G, Baral C. Querying parse tree database of MEDLINE text to synthesize user-specific biomolecular networks. In: Pacific symposium on biocomputing; 2009. p. 87-98). In order to be efficient, these syntactic approaches often rely on large sets of patterns and stable ontologies to guarantee performance on diverse sentence structures. Unfortunately, a systematic catalog of patterns for pharmacogenomics is not available (Dumontier M, Villanueva-Rosales N. Towards pharmacogenomics knowledge discovery on the semantic web. Briefings Bioinform 2009; 100:153-63; Coulet A, Smail-Tabbone M, Napoli A, Devignes M D. Suggested ontology for pharmacogenomics (SO-pharm): modular construction and preliminary testing. In: KSinBIT; 2006, LNCS 4277. p. 648-57).

The Semantic Web community has developed methods for learning ontologies from text using unsupervised approaches (Aussenac-Gilles N, Soergel D. Text analysis for ontology and terminology engineering. Appl Ontol 2005; 1(1):35-46; Buitelaar P, Cimiano P, Magnini B. Ontology learning from text: methods, evaluation and applications, vol. 123 of frontiers in artificial intelligence. IOS Press; 2005). Most of these efforts focus on learning hierarchies of concepts. Ciaramita et al. studied unsupervised learning of relationships between concepts (Ciaramita M, Gangemi A, Ratsch E, Saric J, Rojas I. Unsupervised learning of semantic relations between concepts of a molecular biology ontology. In: IJCAI; 2005. p. 659-64). Their method produces a network of concepts where edges are associated with precise semantics (e.g., Virus encodes Protein).

Other efforts have focused on enriching existing ontologies for NLP using Web content (Ontology Development Information Extraction (ODIE) project: http://www.bioontology.org/ODIE-project, [accessed 02.11.10]). Cilibrasi and Vitányi proposed a method to automatically learn the semantics of processed words, hypothesizing that semantically related words co-occur more frequently in Web pages than do unrelated words (Cilibrasi R, Vitányi PMB. Automatic meaning discovery using Google. In: Kolmogorov complexity and applications; 2006). Gupta and Oates used Web content to identify concept mappings for previously unrecognized words discovered while processing text (Gupta A, Oates T. Using ontologies and the web to learn lexical semantics. In: IJCAI; 2007. p. 1618-23).

SUMMARY OF THE INVENTION

Embodiments of the present invention include methods for the extraction and normalization of relationships from text via ontology induction. In an embodiment, the methods of the present invention process natural language text and identify relationships between drugs, genes, and phenotypes in a manner that is scalable, accurate and exhaustive. The methods of the present invention generalize to other fields such as situations that include text written in complete sentences.

An embodiment of the present invention considers named-entity recognition as the process of identifying members of the lexicon within the text, amidst other words. With such lexicons, there is an opportunity to use syntactic sentence parsers to identify rich rule sets automatically. These rule sets take advantage of sentence structure and grammar to extract more precise information. In addition, these rule sets can be organized in an ontology that allows normalization of relationships and inference over them.

Pharmacogenomics (PGx) is the study of how individual genomic variations influence drug-response phenotypes. PGx knowledge exists for the most part in the scientific literature in sentences that mention relationships. A large fraction of this knowledge can be represented as binary relationships R (a, b), where a, and b are subjects and objects related by a relationship of type R. Sometimes, a and b are instances of a gene (e.g., VKORC1 gene), drug (e.g., warfarin), or phenotype (e.g., clotting disorder). As will be shown in the present disclosure, very often a and b are entities that are modified by genes (e.g., VKORC1 polymorphism), drugs (e.g., warfarin dose) or phenotypes (e.g., clotting disorder treatment). R is a type of relation described by words such as "inhibits", "transports", or "treats" and their synonyms.

Although the three key entities in PGx (genes, drugs, and phenotypes) can be target nouns for relation extraction, they are more often indicators of latent PGx knowledge, as they modify other concepts to create a second set of entities required to precisely describe PGx relationships. These can be called modified entities in contrast with the key entities that modify and expand them. These modified entities can be any biomedical entity, such as a gene variation, drug effect, or disease treatment. For example, the gene entity VKORC1 (a key entity) is used as a modifier of the concept polymorphism in "VKORC1 polymorphisms affect warfarin response," indicating that VKORC1 polymorphism is a critical (composite) PGx entity. This sentence also indicates that a modified entity, warfarin response, will be important as well.

Disclosed herein is a method according to an embodiment of the present invention for using a syntactical parser to identify recurrent binary relationships that express PGx knowledge. Many of these relationships use genes, drugs, and phenotypes as modifiers of other entities. These relationships and the associated entities are organized in an ontology that maps diverse sentence structures and vocabularies to a common semantics. In an embodiment, 87 million sentences were processed using this ontology to capture and normalize more than 40,000 specific PGx relationships. These relationships are summarized in the form of a semantic network (e.g., a network where entities (nodes) and relationships (edges) are associated with the semantics defined in the presently described ontology). They will be useful to assist database curation and as a foundation for knowledge discovery and data mining.

Using an embodiment of the methods of the present invention, entities that are modifications of base terms can be extracted. For example, dosage of a drug as opposed to just the name of a drug. Using embodiments of methods of the present invention as described herein, the sentence structure encoded in the dependency graph resulting from parsing the sentence can be analyzed. In an embodiment, the methods of the present invention are used to analyze the dependency graph data structure created by the Stanford Parser for each sentence. This is used to extract the raw relationship between (1) subject and (2) object of a (3) relationship.

The present invention includes methods for the creation of an ontology. These methods provide a rich, semantically precise ontology for Pharmacogenomics, where none previously existed and allows the normalization of the identified entities and relationships into a common framework. These aspects of the presently described method generalize to any domain of interest in which the goal is to extract relationships between base entities of interest.

Embodiments of the present invention have at least the following advantages and improvements over existing methods:

Key entities (such as drugs, genes) are identified along with the terms that modify these entities. As a result, the methods of an embodiment of the present invention are able to recognize and expanded sets of entities which are of specific interest (such as the dosage of a drug, the level of expression of a gene, among other things). The specific relationship is often that between these expanded entities declared by the modifications of the seed terms. Such relationships are captured by identification of seed terms alone using methods of the present invention.

The methods of embodiments of the present invention do not require a pre-specification and enumeration of relationships to identify in the text. Current methods, on the other hand, typically restrict identifiable relationships to a set of pre-specified relationships. Such pre-specification of allowable relationships is time-consuming, non-robust, and infeasible given the multiple types of relationships that exist in natural language textual documents.

Extracted terms and relationships are normalized to map concepts into a common framework with precisely defined semantics specified in an ontology. An embodiment of the present invention includes methodologies for the creation of an ontology.

These and other embodiments can be more fully appreciated upon an understanding of the detailed description of the invention as disclosed below in conjunction with the attached figures.

BRIEF DESCRIPTION OF THE DRAWINGS

The following drawings will be used to more fully describe embodiments of the present invention.

FIG. 10 (Table 1) is a summary of an algorithm traversing the dependency graph from entities through root to other entities according to an embodiment of the present invention.

FIG. 11 (Table 2) is a summary of the 30 most frequent relationship types and entities modified by genes, drugs or phenotypes according to an embodiment of the present invention.

FIG. 12 (Table 3) is a tabulation of percentages of raw relationships covered using the 100 and 200 most frequent relationship types and entities according to an embodiment of the present invention.

FIG. 13 (Table 4) is a tabulation of the 15 most instantiated normalized roles (first column) and normalized concepts modified by gene (second column), drug (third column), and phenotype (fourth column) in the knowledge base according to an embodiment of the present invention.

DETAILED DESCRIPTION OF THE INVENTION

Figure 14:
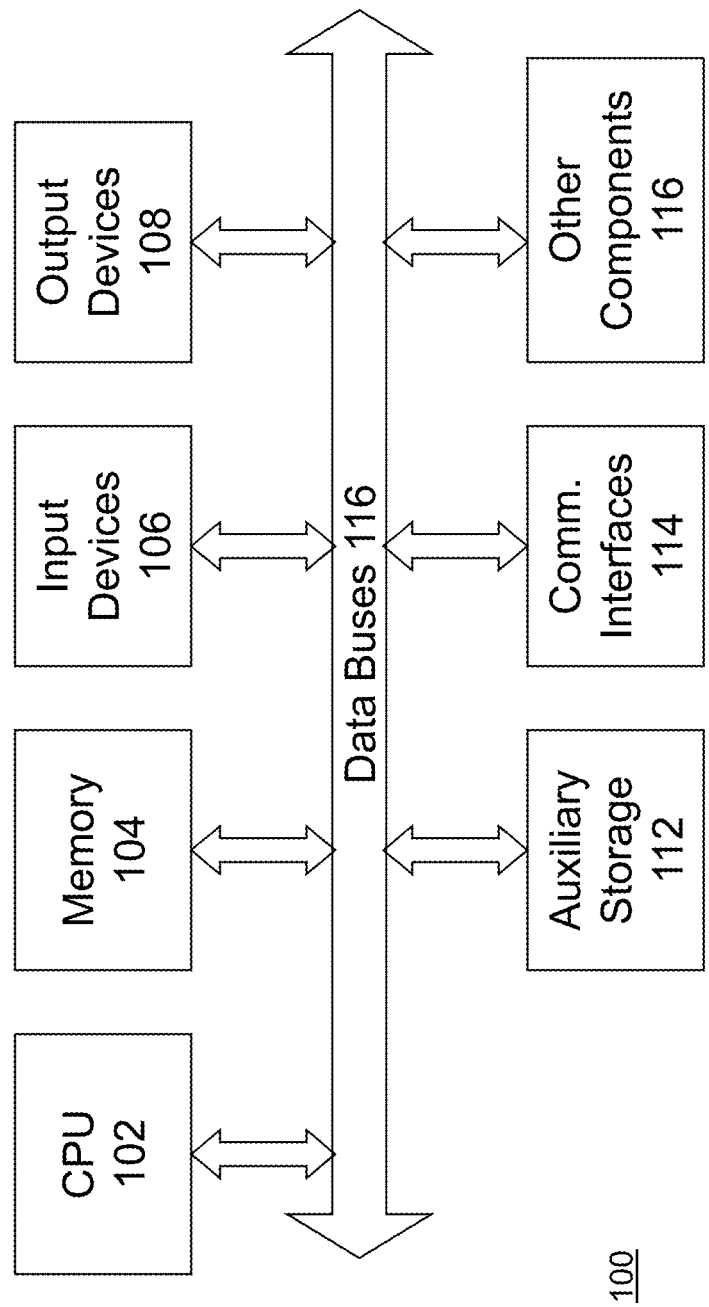
FIG. 14 is a block diagram of a computer system on which the present invention can be implemented.

Among other things, embodiments of the present invention relate to methods, techniques, and algorithms that are intended to be implemented in a digital computer system 100 such as generally shown in FIG. 14. Such a digital computer is well-known in the art and may include the following.

Computer system 100 may include at least one central processing unit 102 but may include many processors or processing cores. Computer system 100 may further include memory 104 in different forms such as RAM, ROM, hard disk, optical drives, and removable drives that may further include drive controllers and other hardware. Auxiliary storage 112 may also be include that can be similar to memory 104 but may be more remotely incorporated such as in a distributed computer system with distributed memory capabilities.

Computer system 100 may further include at least one output device 108 such as a display unit, video hardware, or other peripherals (e.g., printer). At least one input device 106 may also be included in computer system 100 that may include a pointing device (e.g., mouse), a text input device (e.g., keyboard), or touch screen.

Communications interfaces 114 also form an important aspect of computer system 100 especially where computer system 100 is deployed as a distributed computer system. Computer interfaces 114 may include LAN network adapters, WAN network adapters, wireless interfaces, Bluetooth interfaces, modems and other networking interfaces as currently available and as may be developed in the future.

Computer system 100 may further include other components 116 that may be generally available components as well as specially developed components for implementation of the present invention. Importantly, computer system 100 incorporates various data buses 116 that are intended to allow for communication of the various components of computer system 100. Data buses 116 include, for example, input/output buses and bus controllers.

Indeed, the present invention is not limited to computer system 100 as known at the time of the invention. Instead, the present invention is intended to be deployed in future computer systems with more advanced technology that can make use of all aspects of the present invention. It is expected that computer technology will continue to advance but one of ordinary skill in the art will be able to take the present disclosure and implement the described teachings on the more advanced computers or other digital devices such as mobile telephones or "smart" televisions as they become available. Moreover, the present invention may be implemented on one or more distributed computers. Still further, the present invention may be implemented in various types of software languages including C, C++, and others. Also, one of ordinary skill in the art is familiar with compiling software source code into executable software that may be stored in various forms and in various media (e.g., magnetic, optical, solid state, etc.). One of ordinary skill in the art is familiar with the use of computers and software languages and, with an understanding of the present disclosure, will be able to implement the present teachings for use on a wide variety of computers.

The present disclosure provides a detailed explanation of the present invention with detailed explanations that allow one of ordinary skill in the art to implement the present invention into a computerized method. Certain of these and other details are not included in the present disclosure so as not to detract from the teachings presented herein, but it is understood that one of ordinary skill in the art would be familiar with such details.

Methods

A method according to an embodiment of the present invention is described for relationship extraction that uses (1) syntactic rules to extract relationships and (2) a learned ontology to normalize those relationships. One of ordinary skill in the art will understand, however, that the teachings of the present invention are not limited to the disclosed embodiments. Indeed, the present invention extends to many other applications as would be known to those of ordinary skill in the art.

Figure 1A:
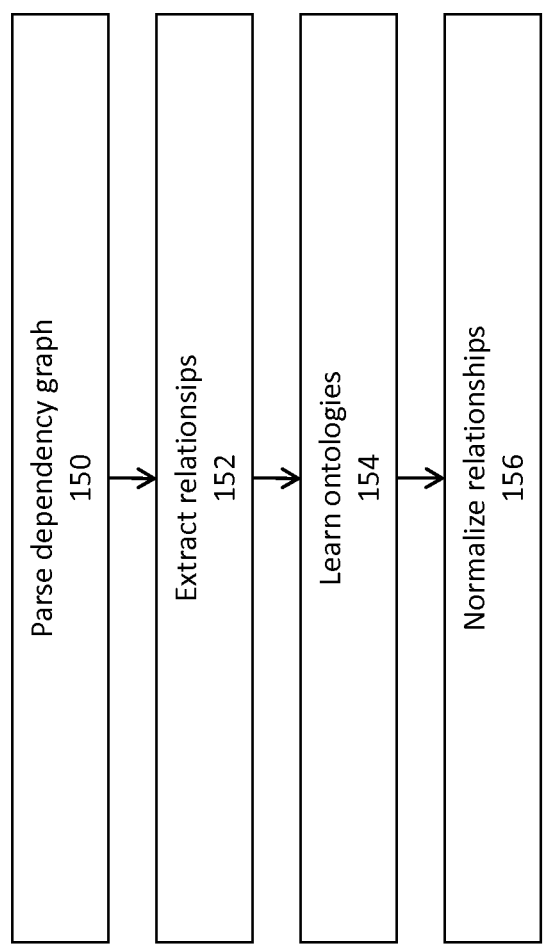
FIG. 1A is a flowchart describing a method according to an embodiment of the present invention for extracting pharmacogenomics (PGx) relationships from text.

Shown in FIG. 1A is a flowchart describing a method according to an embodiment of the present invention for extracting pharmacogenomics (PGx) relationships from text. In an embodiment of the present invention, at step 150, text is parsed. As describe herein, an embodiment of the present invention uses text from MEDLINE abstracts, but one of ordinary skill in the art would understand that many other types of text can be used in accordance with the teachings of the present invention. Also in an embodiment described herein, the Stanford Parser is used. In its use as described herein, it yields a Dependency Graph (DG) data structure that provides a syntactical structure of each sentence. In an embodiment, at step 152, relationships are extracted from the Dependency Graphs. For example, PGx entities and their raw relationships are identified. In a certain sense, the relationships are "raw" because their subject, object, and type use natural language terms. At step 154, the extracted relationships are processed to build (e.g., first run) or refine (e.g., subsequent runs) an ontology of PGx relationships. In an embodiment, a first run though the algorithm can be used to build an ontology of PGx relationships. Subsequent runs can then refine the ontology. At step 156, each of the raw relationships are mapped to the ontology and are expressed in a normalized form. In an embodiment, normalized relationships create a network in which nodes are PGx entities and edges are relationships, both of which are associated with precise semantics.

Figure 1B:
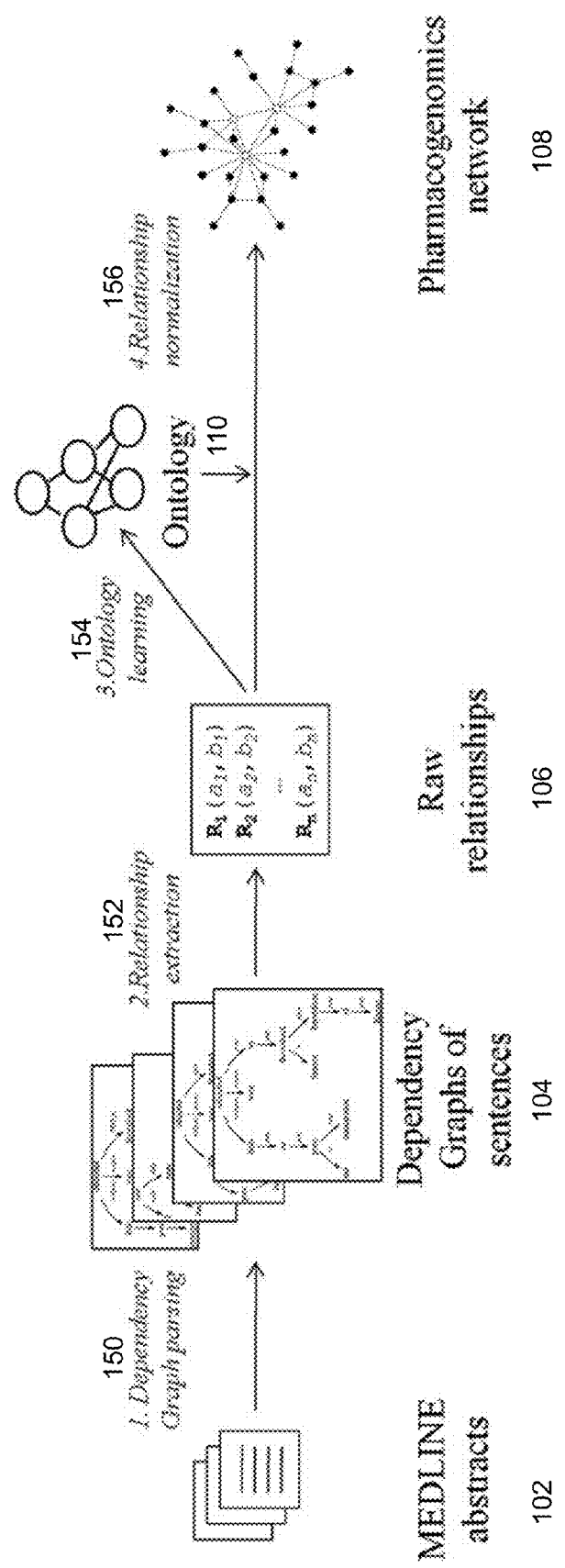
FIG. 1B is a flow diagram according to an embodiment of the present invention for extracting pharmacogenomics (PGx) relationships from text.

To further assist in understanding the present invention, FIG. 1B presents a flow diagram according to an embodiment of the present invention. As shown, an input is a corpus of article abstracts 102 split into individual sentences. Certain prior art makes such a corpus available and also provides a way to retrieve the sentences (Xu R, Supekar K, Morgan A, Das A, Garber A. Unsupervised method for automatic construction of a disease dictionary from a large free text collection. In: AMIA Annu Symp Proc 2008; 2008. p. 820-824). Lexicons of PGx key entities (drugs, genes, and phenotypes) from PharmGKB (http://www.pharmgkb.org/resources/downloads and web services.jsp) are used to retrieve sentences mentioning pairs of key entities. Retrieved sentences are parsed (step 150) with the Stanford Parser and represent the sentence using a convenient data structure called a "Dependency Graph" 104 (Klein D, Manning C D. Accurate unlexicalized parsing. In: ACL; 2003. p. 423-30). Each retrieved sentence is analyzed to extract the raw relationships (step 152) between key entities themselves or other entities that they modify to produce the collection of raw relationships 106.

After applying this procedure to many pairs of key entities (step 154) to develop an ontology 110, the raw relationships and entities are gathered and mapped (step 156) to a much smaller set of "normalized" relationships 108 and entities based on synonymy, arranged hierarchically in an OWL ontology (OWL (Web Ontology Language): http://www.w3.org/TR/owl-features/). This ontology is assumed to be representative of PGx relationships. This ontology can then be applied to all raw relationship instances in the corpus to create a very large set of normalized relationships representing the semantic content of the corpus.

Sentence Parsing of MEDLINE into Dependency Graphs

In an embodiment, an objective of sentence parsing is to provide, in a format that is easy to process, the syntactical structure of sentences that potentially mention a PGx relationship. Focus is placed on sentences that mention at least two PGx key entities. An index was used of individual sentence of MEDLINE abstracts published before 2009 (17,396,436 abstracts and 87,806,828 sentences) processed by Xu et al. (Xu R, Supekar K, Morgan A, Das A, Garber A. Unsupervised method for automatic construction of a disease dictionary from a large free text collection. In: AMIA Annu Symp Proc 2008; 2008. p. 820-824). This index has been built on the full text of sentences with the Lucene library and can consequently be queried with any term (Agichtein E, Gravano L. Snowball: extracting relations from large plaintext collections. In: ACM DL; 2000. p. 85-94). It returns sentences that have been indexed with the query terms and also returns "parse trees" that correspond to retrieved sentences.

A parse tree is a rooted tree that represents the syntactical structure of a sentence. Shown in FIG. 2. is an example of a parse tree 200 of the sentence "Several single nucleotide polymorphisms (SNPs) in VKORC1 are associated with warfarin dose across the normal dose range" (PubMed ID 17161452). For convenience in understanding parse tree 200, the words of the sentence at issue are denoted as follows: Several 202, single 204, nucleotide 206, polymorphisms 208, SNPs 210, in 212, VKORC1 214, are 216, associated 218, with 220, warfarin 222, dose 224, across 226, the 228, normal 230, dose 232, range 234. This parse tree is obtained when querying an index (built in previous work) with query (1) that looks for two pharmacogenomics key entities: VKORC1 (a gene) and warfarin (a drug). Parse trees were previously generated by applying the Stanford Parser on every sentence.

The Stanford Parser is a statistical natural language parser (Klein D, Manning C D. Accurate unlexicalized parsing. In: ACL; 2003. p. 423-30). It uses a set of training sentences in which the grammatical function of words were annotated by experts to record the most likely syntactical structure of a sentence. Parse trees of sentences that mention at least two PGx key entities are subsequently transformed into Dependency Graphs (DGs) with the same Stanford Parser (Agichtein E, Gravano L. Snowball: extracting relations from large plaintext collections. In: ACM DL; 2000. p. 85-94). This DG format provides the syntactical structure of sentences were analyzed to extract relationships.

Querying the Sentence Index Using Seeds

From the corpus, only sentences with pairs of PGx key entities, (e.g., one gene and one drug, or one gene and one phenotype) are considered. For this initial work, focus was not placed on drug-phenotype pairs because they are numerous, and the majority of these pairs are not of PGx interest. For example, to retrieve sentences that potentially mention a relationship between the gene VKORC1 and the drug warfarin, the index was queried with two sets of synonyms as follows:

(VKORC1OR VKOR OR VKCFD2) AND (warfarin OR Coumadin). (1)

Figure 2:
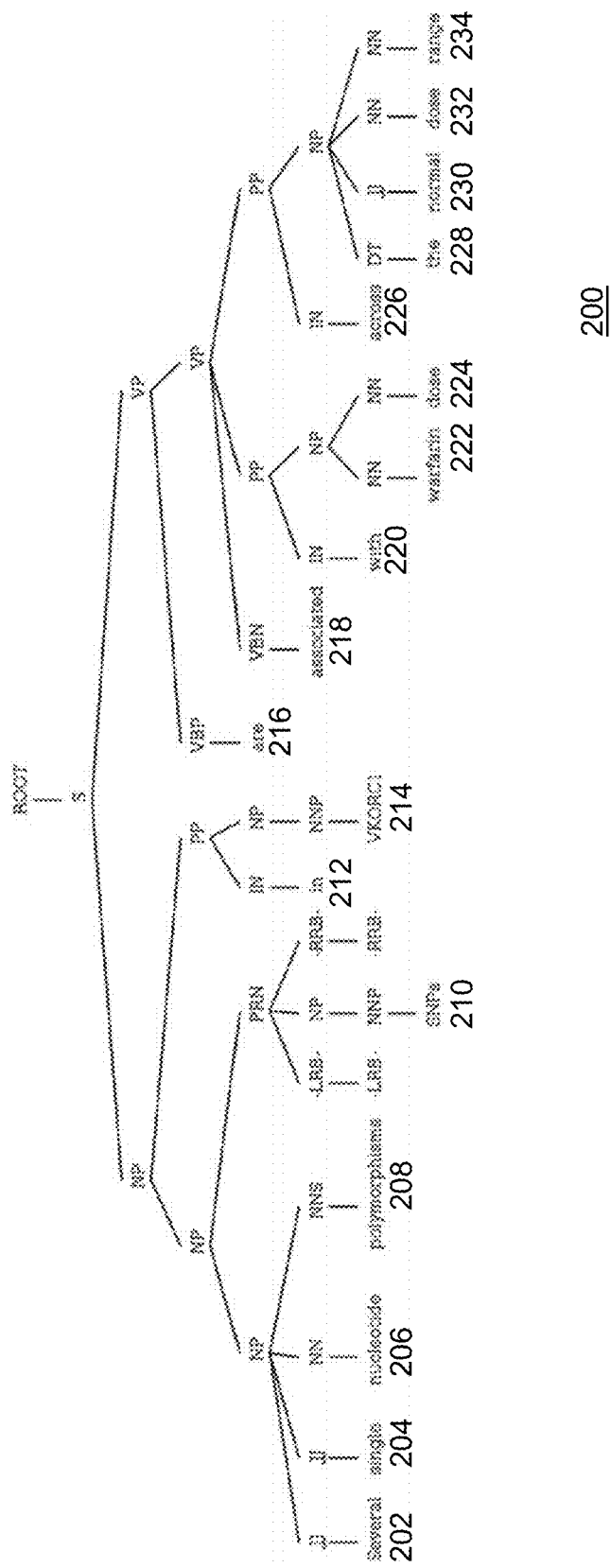
FIG. 2 is an example of a parse tree of the sentence "Several single nucleotide polymorphisms (SNPs) in VKORC1 are associated with warfarin dose across the normal dose range" according to an embodiment of the present invention.

Results of these queries were sentences (and corresponding parse trees) mentioning at least two terms, one that refers to the first entity and one that refers to the second entity. Sets of synonyms used to build such queries are from the PharmGKB lexicons. For this initial work, 41 important genes were used, highlighted by PharmGKB (http://www.pharmgkb.org/search/annotatedGene), as well as 3007 drugs and 4202 phenotypes. Drug and phenotype names listed in lexicons are not restricted to PGx. Phenotype names include disease and adverse reaction names. Querying the index with pairs of entities named in such lexicons can be considered as a task of named-entity recognition. In one retrieved sentence (and in its corresponding parse tree), the two particular terms, called seeds, that correspond to the two recognized entities were distinguished. These are called seeds because they form the basis for relationship extraction. Seeds of the parse tree shown in FIG. 2 are VKORC1 214 and warfarin 224.

Reducing the Set and the Size of Parse Trees

In order to reduce computational complexity, the number of considered parse trees or parse tree fragments was reduced. The relative positions of the two seeds in the sentences clauses was compared. A clause is a group of terms of a sentence. Some sentences contain several independent clauses. For example the sentence "I am a doctor, and my wife is a lawyer" has two independent ones.

If the two seeds are not located in the same clause of the sentence, the parse tree is removed from consideration (the seeds are unlikely to have an extractable relationship across clauses). If the parse tree contains more than one clause, and a clause does not contain both seeds, then the clause is pruned (only clauses containing more than two seeds are kept). For example, parse tree 200 in FIG. 2 contains only one clause with both seeds and was neither removed from consideration nor pruned.

Transformation of Parse Trees into Dependency Graph

Figure 3:
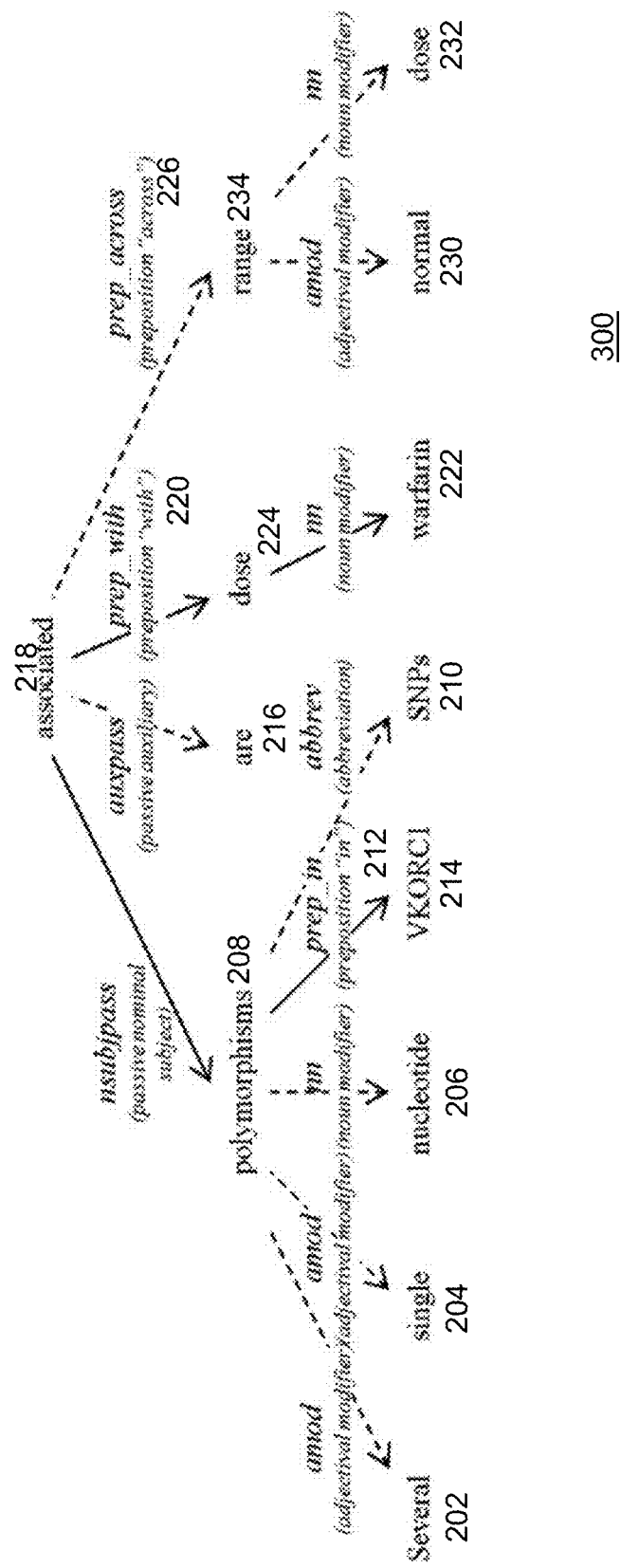
FIG. 3 is an example of a dependency graph of the sentence "Several single nucleotide polymorphisms (SNPs) in VKORC1 are associated with warfarin dose across the normal dose range" according to an embodiment of the present invention.

The Stanford Parser summarizes the syntactical structure of a parse tree in an easy to process format, called a Dependency Graph (DG) (de Marneffe M-C, Manning CD. The Stanford typed dependencies representation. In: COLING workshop on cross-framework and cross-domain parser evaluation; 2008). DGs are rooted, oriented, and labeled graphs, where nodes are words and edges are dependency relations between words (e.g., noun modifier, nominal subject). FIG. 3 shows the DG built from parse tree 200 shown in FIG. 2. According to an embodiment of the present invention as shown in FIG. 3, the Stanford Parser creates a Dependency Graph (DG) data structure from a parse tree such as parse tree 200 in FIG. 2. As shown in FIG. 3, Dependency Graph 300 corresponds to the sentence "Several single nucleotide polymorphisms (SNPs) in VKORC1 are associated with warfarin dose across the normal dose range." For convenience in understanding dependency graph 300, the words of the sentence at issue are denoted the same as in FIG. 2: Several 202, single 204, nucleotide 206, polymorphisms 208, SNPs 210, in 212, VKORC1 214, are 216, associated 218, with 220, warfarin 222, dose 224, across 226, the 228, normal 230, dose 232, range 234. This parse tree is obtained when querying an index with a query (1) that looks for two pharmacogenomics key entities: VKORC1 214 (a gene) and warfarin 222 (a drug). As shown for dependency graph 300, its two seeds are VKORC1 214 and warfarin 222, and its root is associated 218. Solid lines in FIG. 3 represent the path that connects both seeds to each other via the root. This path is used in the next step to extract the following raw relationship: associated (VKORC1_polymorphisms, warfarin_dose).

DGs are easier to read and process than parse trees or other representations. Relationships between sentence words are binary, and they occur directly between "content" words (e.g., "associated" is connected directly to "dose"), rather than being mediated indirectly via less important function words (e.g., "associated" is related to "dose" via a common link to "with"). Each DG includes a root (or head) that enables easy recognition of the subject and the object of a sentence. DGs highlight semantic content and are relatively easy to understand.

Relation Extraction

The second step of the described method uses syntactic structure provided by DGs to identify raw relationships of the form R (a, b) where:

a and b are two paths (e.g., sequences of nodes) in a DG, each of which is either a single key entity (an instance of gene, drug or phenotype) or of a modified entity—an entity that is not a gene, drug or phenotype but is modified by one (e.g., an instance of gene variation, drug dose or phenotype treatment);

R is a node in the DG that connects a and b, and indicates the nature of their relationship.

In the example shown in FIG. 3, a is "VKORC1 polymorphisms", b is "warfarin dose," and R is "associated." An algorithm is defined that extracts relationships from the DG that correspond to the two following patterns:

verb(seedA_expanded; seedB_expanded) (2)

nominalized_verb(seedA_expanded; seedB_expanded) (3)

An expanded seed is a seed that matches the input key entity or that represents a modified entity in which the key entity modifies another entity. The relations are captured by verbs or nominalized versions of verbs (such as "association" that is the nominalized version of "associate"). This algorithm has three steps: seed recognition, seed expansion, and coupling of expanded seeds, described as follows.

Seed Recognition

Seeds are identified using the input lexicons. The PharmGKB lexicons are used for genes, drugs and phenotypes that include a basic list of synonyms. Seeds may be a single word or a compound noun. This "seed recognition" step localizes the two seeds in the DG. When a seed is composed of one word, (e.g., thrombosis), the system uses string matching and techniques to handle plural and of capitalized forms. If a seed is composed of more than one word (e.g., venous thromboembolism), a DG for the seed itself (noted as DGseed) is created and the parsed sentence DG is examined to identify the subset of nodes matching the DGseed.

Seed Expansion

The DG has information that allows the expansion of the seed to determine if it is being used as a key entity or a modified entity. A seed is expanded by traversing edges of the DG. The method of traversal is defined by the types of dependencies that connect the seed to other concepts. Depending on these dependencies (Table 1 shown in FIG. 10) summarizes the decision logic), the algorithm will:

(i) expand the seed (continuing traversing the DG and constructing the seed);

(ii) end the expansion by detecting a relationship type represented by a verb (e.g., activate, bind, and regulate) or a nominalized form of a verb (e.g., activation, binding, and regulation). The type of the dependency determines whether the seed is the subject or object in the relationship;

(iii) interrupt the expansion if neither (i) nor (ii) applies.

Table 1 (shown in FIG. 10) is a summary of the algorithm traversing the dependency graph from entities through root to other entities according to an embodiment of the present invention. The subject and object may be modified entities, and the dependency graph provides data types that help decide how to construct the subject, object, and relationship for each graph. In particular, depending on the type associated with each edge in the graph during traversal of a DG, the seed expansion either (i) continues, (ii) ends and thereby establishes a subject or an object, or (iii) interrupts. To identify a relationship, the expansion of the two seeds has to end (one as a subject and one as an object) on a common "root" word.

Seed Coupling

Figure 4:
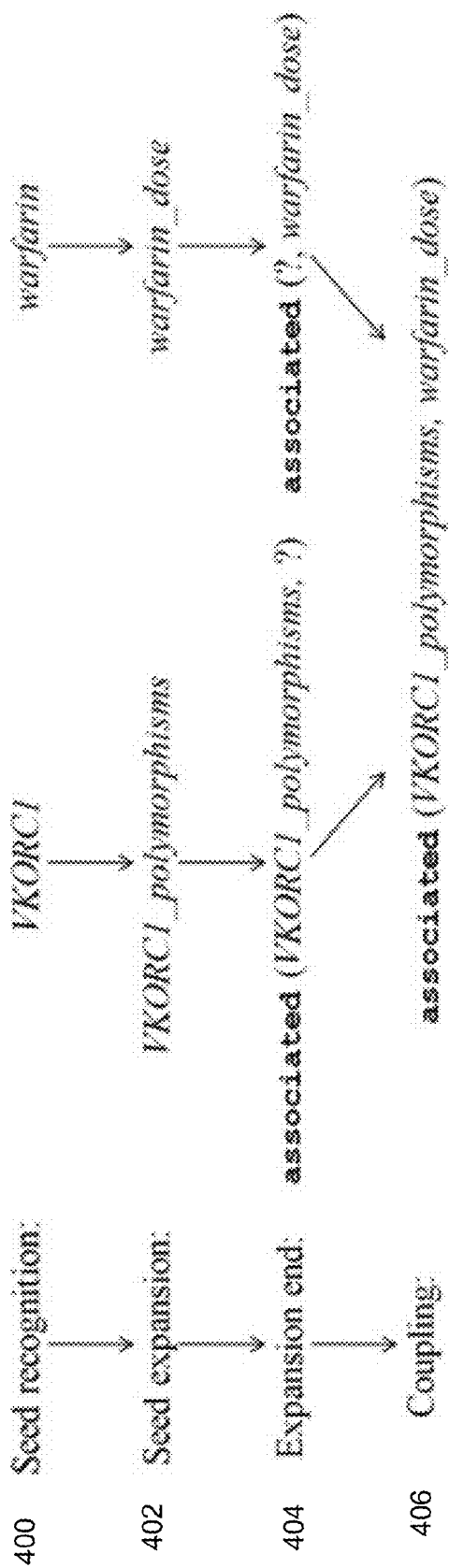
FIG. 4 is a flow diagram of certain steps according to an embodiment of the present invention for recognizing and expanding two seeds.

When two expanded seeds (one subject expanded seed and one object expanded seed) each end by reaching the same verb or nominalized verb, they are associated to create a raw relationship, as subject or object depending on the dependency type. FIG. 4 illustrates the expansion and subsequent coupling of seeds recognized in the DG shown in FIG. 3. More particularly, shown in FIG. 4 are certain steps of recognizing and expanding the two seeds in the example sentence shown in FIGS. 2 and 3 that include seed recognition 400 where the seeds VKOCR1 and warfarin are recognized; seed expansion 402, expansion end 404, and coupling 406 that yields associated (VKOCR1_polymorphisms, warfarin,_dose). Starting with the seed entities, VKOCR1 and warfarin, the rules provided in Table 1 (FIG. 10) are used to traverse the Dependency Graph 300 in FIG. 3 to recognize the subject (VKORC1_polymorphisms), object (warfarin_dose) and relationship (associated) in the Dependency Graph.

Evaluation of Raw Relationship Precision

The precision of extracting raw relationships was evaluated. A subset of 220 raw relationships were selected and classified into three categories: complete and true, incomplete and true, and false. Incomplete and true relationships are relationships that are consistent with mentioned relationships but are missing partial information. It is then required that the lack of information does not change the interpretation of the relationship. For example, if derived from the sentence "polymorphisms in VKORC1 are associated with warfarin dose":

associated (VKORC1_polymorphisms, warfarin_dose) would be complete and true;

associated (VKORC1_polymorphisms, warfarin) would be incomplete and true;

polymorphisms (VKORC1, warfarin_dose) would be false.

Ontology Construction

Raw relationships represent multiple equivalent ways to express a relationship. In order to simplify the analysis of the semantics, many raw relationships must be mapped onto a smaller, normalized set of relationships. The raw relationships observed in the text were examined and grouped into a hierarchical domain ontology of PGx relationships. The most frequent relationship types were identified and then similar ones were merged and organized hierarchically. Modified entities were also tracked and merged. The number of raw entity and relationship types were computed. The number of normalized types resulting from grouping them was also computed. The steps of ontology construction are described here. In an embodiment, this construction is carried out once, at the first iteration of the approach, but the ontology can be refined during subsequent iterations.

Identification of Relationship Types

Figure 5:
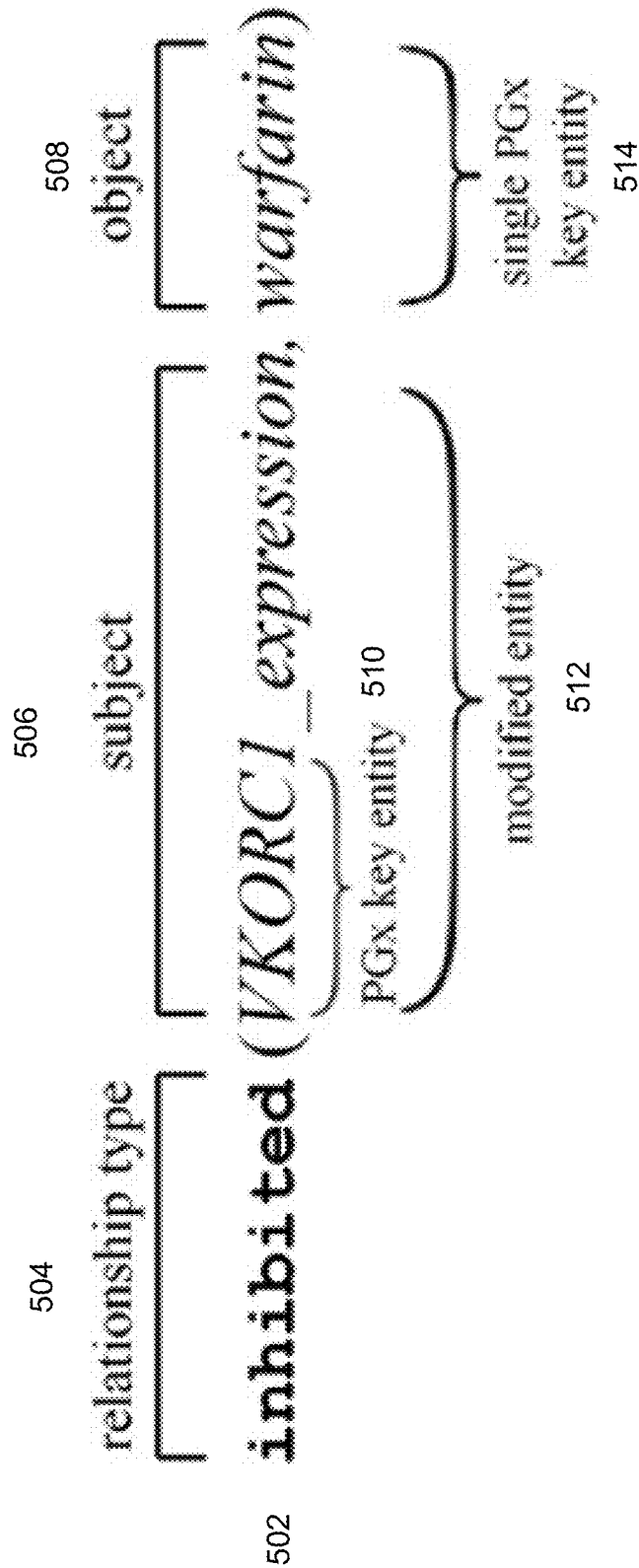
FIG. 5 illustrates a raw relationship derived from a dependency graph according to an embodiment of the present invention.

Four lists were created from the raw relationships extracted from the DGs. The lists represent (1) the most frequent types of relationships and the most frequently modified entities modified by (2) genes, (3) drugs, and (4) phenotypes as defined in the lexicons for these entities as shown in FIG. 5. Each list is processed to remove word heterogeneity caused by captions, plurals, and conjugations. Equivalent words were then combined and their frequency of occurrence was computed to produce a list sorted by frequency of use. Modified entities are the subjects or objects of relationships (e.g., a or b) grammatically modified by either a gene, a drug, or a phenotype.

As shown in FIG. 5, a raw relationship 502 that is derived from the dependency graph has three components: relationship type 504, subject 506, and object 508. Both subject 506 and object 508 can be either a single PGx key entity 510 and 514 or a modified entity 512 using the key entity as a modifier (e.g., VKORC1_expression).

Organization of Relationship Types and Entities in Hierarchies

Figure 6:
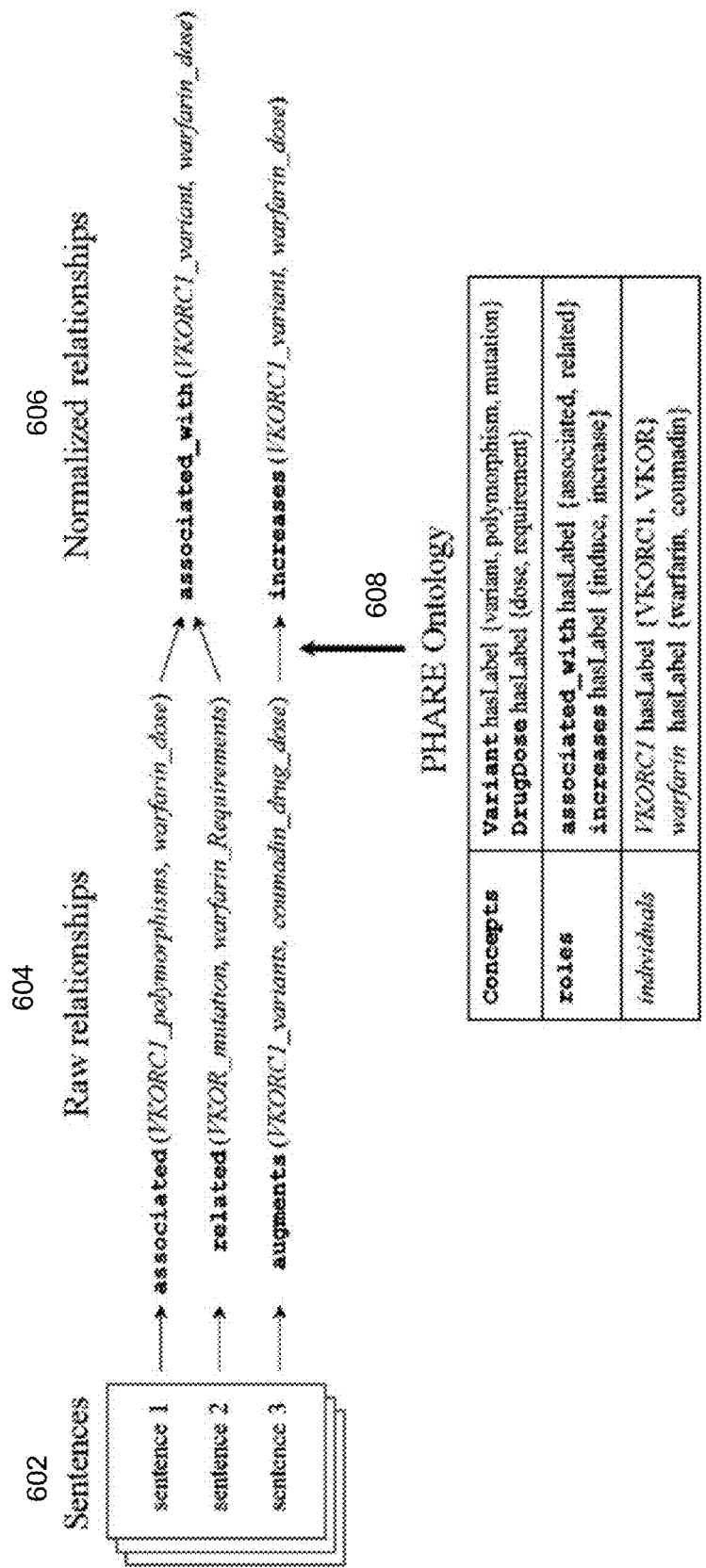
FIG. 6 is a flow diagram of how sentences are used to form raw relationships to then form normalized relationships according to an embodiment of the present invention.

Elements of each list were examined and grouped into sets of synonyms and then organized into role and concept hierarchies. Shown in FIG. 6 is an example of roles and concepts that take sentences 602 to form raw relationships 604 to then form normalized relationships 606. More particularly, shown are three raw relationships 610, 612, and 614 normalized to two normalized expressions 616 and 618, using the PHARE (PHArmacogenomics RElationship) ontology 608 of entities and relationships. In this example, the first two raw relationships 610 and 612 express the same relationship 616 according to the mappings in the presently described ontology (e.g., drug dose and drug requirement are declared synonyms in the ontology). The third raw relationship 614 maps to a more specific relationship (increases) 618 that is a child of the more general (associated) relationship.

Relationship synonyms (e.g., decrease, reduce) represent roles in the ontology. A role is a binary relation associated with a domain and a range. It is named with one of the synonyms (e.g., decrease) and associated with labels that correspond to the other synonyms. The roles are organized in a hierarchy so that any instance of a role (e.g., inhibit) is also an instance of its parent (less precise) role (e.g., affect).

Terms that are modified by the same kind of entity (e.g., gene) are grouped into sets of synonyms (e.g., polymorphism, mutation, and variant) and lead to the creation of concepts in the ontology. A concept is named with one of the synonyms as a reference to label the group as a whole (e.g., the variant label leads to the concept name Variant) and is associated with all the other synonym labels. Distinct concepts are organized in a concept hierarchy such that any instance of a concept (e.g., Variant) is also an instance of its parent concepts (e.g., GenomicVariation).

Importantly, when a new concept is created, it is associated with a description that specifies whether it is modified by genes or drugs or phenotypes. For example, the mention of a genomic variation in text can be modified by a gene name. The Variant concept (with alternate labels "polymorphism" and "mutation") is, therefore, associated with a description stating that instances of Variant can be modified by instances of Gene. Such a description enables "VKORC1 polymorphism" in text to be mapped to the concept Variant, since modified by a gene name (VKORC1) whereas the phrase "important polymorphism" is not mapped, since "important" is not an instance of the Gene concept.

The ontology was represented in description logic and encoded in OWL using Protégé (Baader F, Calvanese D, McGuinness D L, Nardi D, Patel-Schneider P F. The description logic handbook. Cambridge University Press; 2003; [30] (Knublauch H, Fergerson R W, Fridman Noy N, Musen M A. The Protégé OWL plugin: an open development environment for semantic web applications. In: ISWC; 2004. p. 229-43). The ontology was built once, examined and validated by three domain experts (curators at PharmGKB). Because only the first 200 elements of each of the four lists were considered, the ontology construction and examination took approximately 4 hours (approximately 1 hour per list).

Relationship Normalization

Once the ontology is built, it can be used to map most raw relationships to common semantics. The mapping process has two steps: (1) entity names are normalized, and then (2) relationships are normalized. Normalization is a many-to-one mapping that maps multiple diverse textual statements to a common normalized form. FIG. 6 illustrates the normalization process.

Normalization of Entity Names

To name modified entities uniformly, an algorithm was implemented that takes a modified entity name of any length and returns its normalized form according to the ontology. Initially, the modified entity was decomposed into its original seed and the other words in the string. The algorithm iterates over these words to construct the normalized name of the entity. The first word is the seed.

Using the PharmGKB lexicons, seeds are a gene, drug, or phenotype (e.g., VKORC1, warfarin, or bleeding), and they are associated with a concept C seed. With Cseed determined, the next word is processed. A match is sought between the next word and labels of concepts that are modified by Cseed, according to the ontology. If a concept matches, the processed word is associated with this new concept. In the case where no match is found, a match is searched between the processed word and labels of concepts that are modified by more general concepts (e.g., those modified by parents of Cseed).

In the case where no further match is found, no concept in the ontology corresponds and then a new concept is created with the processed word as a label and with a description specifying that it is modified by C seed (e.g., $modified.Cseed). This operation is iterated for each successive word of the modified entity, each time assigning the right concept to the new processed word.

When the last word is reached, the normalized version of the entity name is proposed as the concatenation of the seed plus the names of successive assigned concepts. For example, with the modified entity VKORC1_polymorphisms, VKORC1 is the seed and Cseed is the concept Gene. The next word is polymorphism, which refers to a concept modified by Gene. Polymorphism is a synonym of the concept Variant, which is associated with the processed word. Because there are no other words in the modified entity, the normalized name is VKOCR1_variant. When the subject or the object of a raw relationship is a single PGx key entity (gene, drug, phenotype), PharmGKB lexicons provide the normalized name, which is the preferred name of the seed (e.g., VKORC1 for VKOR).

Figure 7:
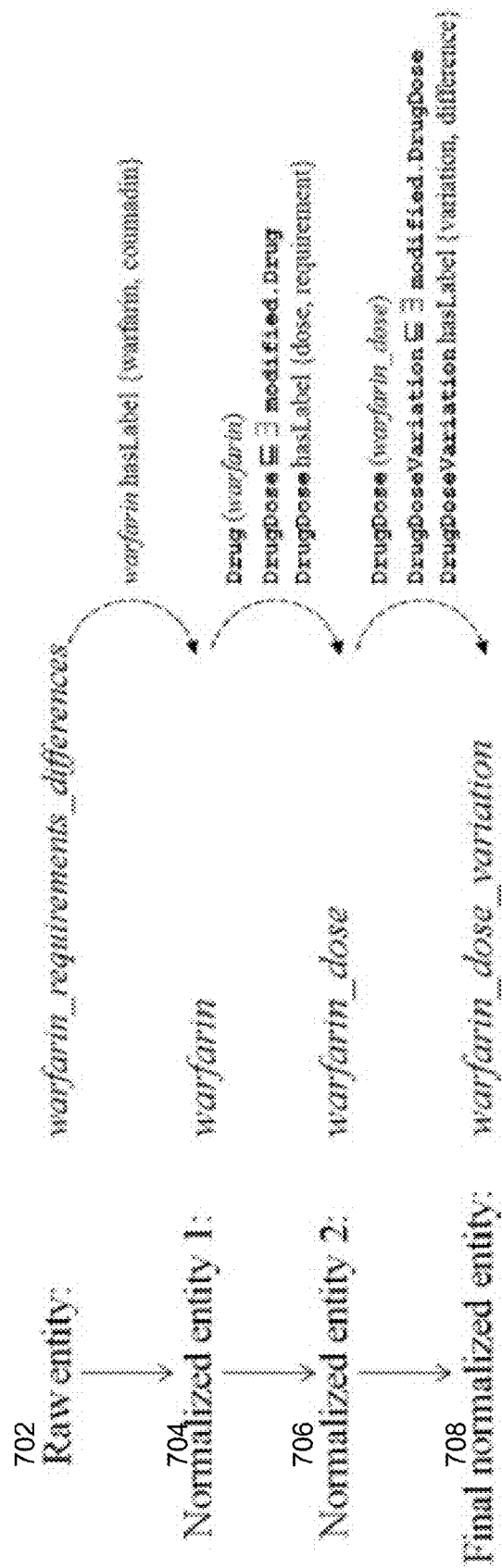
FIG. 7 is an example of a decomposition of certain steps of the normalization of a modified entity made of three words according to an embodiment of the present invention.

Shown in FIG. 7 is a decomposition of certain steps of the normalization of a modified entity made of three words according to an embodiment of the present invention. As shown, starting with the text "differences in warfarin requirements," the raw entity "warfarin_requirements_differences" is extracted 702 and then normalization 704, 706, and 708 is applied using the PHARE ontology. The first normalization 704 ensures that the standard name for warfarin is used (here, Coumadin would have been mapped to warfarin, had it been used). Warfarin is the seed and the concept associated with it, noted Cseed, is Drug according to the ontology. The second normalization 706 maps "requirements" to the standard ontological concept of dose. The final normalization 708 in this embodiment maps "differences" to the ontology concept of variation. Having learned these mappings on the initial training corpus, they can be applied broadly and prospectively to new sentences.

Normalization of Relationship Types

Relationship types are normalized by searching for a role label that matches the raw relationship. If a label matches, the identifier of the corresponding role becomes the normalized type. For example, the type "related," mentioned in FIG. 6, matches to the role associated_with. Normalized entities and relationships are combined to form the normalized relationship. Normalized relationships are used to instantiate concepts and roles from the ontology to create a knowledge base of PGx relationships. Each relationship in the knowledge base is made by the instantiation of:

two concepts (e.g., Variant(vkorcl_variant) and DrugDose (warfarin_dose)) and one role (e.g., associated_with (vkorcl_variant, warfarin_dose)).

A detailed description of the normalization algorithm is provided in Coulet et al. (Coulet A, Altman R B, Musen M A, Shah N H. Integrating heterogeneous relationships extracted from natural language sentences. In: Proceedings of the bio-ontologies SIG, ISMB; 2010) herein incorporated by reference for all purposes.

Results 87,806,828 parse trees were queried to find a total of 295,569 sentences with pairs of PGx entities as seeds. These sentences were pruned to extract 41,134 raw relationships, including 21,050 relationships seeded by gene-drug pairs and 20,084 by gene-phenotype pairs. Table 2 (FIG. 11) shows the relationship types and entities most frequently found in these raw relationships (complete lists are available at http://www.stanford.edu/~coulet/material/entity_lists/). Numbers correspond to their frequency of occurrence in 41,134 raw relationships extracted from 17,396,436 MEDLINE abstracts. Entities can be composed of one or several words.

Shown in Table 3 (FIG. 12) is a tabulation of percentages of raw relationships covered using the 100 and 200 most frequent relationship types and entities according to an embodiment of the present invention. The variable n represents the number of distinct types or entities identified in all relationships. For example, the top 200 entities modified by genes account for 85% of all raw gene-related entities mentioned in the corpus. Similarly, the top 200 relationship types account for 80% of all raw relationships in the presently described corpus.

It was found that the 200 most frequent raw relationship types summarize 80% of extracted relationships (see Table 3 (FIG. 12)). Evaluation of 220 raw relationships indicated that 70% of those were complete true positives, 87.7% were complete or incomplete true positives, and 12.3% were false positives. Distinction between complete and incomplete true positive is described further below.

An ontology of the 200 most frequent relationship types were created and entities called PHARE (PHArmacogenomics Relationships, available at http://www.stanford.edu/~coulet/material/ontology/phare.owl) were modified. PHARE is made of 237 concepts and 76 roles. PHARE concepts are instantiated with 26,966 distinct entities and PHARE roles are instantiated with 46,523 explicit (those are considered explicit in contrast with inferred instantiations that can be considered implicit) relationships between pairs of entities. The number of role instantiations is greater than the number of raw relationships because both role and inverse role instantiations (e.g., R(a, b) and R⁻(b, a)) are counted. Finally, one role instantiation can be supported by several sentences and one entity can be involved in several role instantiations.

Table 4 presents a list of the most commonly used concepts and roles. Numbers to the left represent the number of instances of the role or entity in 41,134 raw relationships. The number in brackets is the number of unique instances of concepts used in these raw relationships.

Figure 8A:
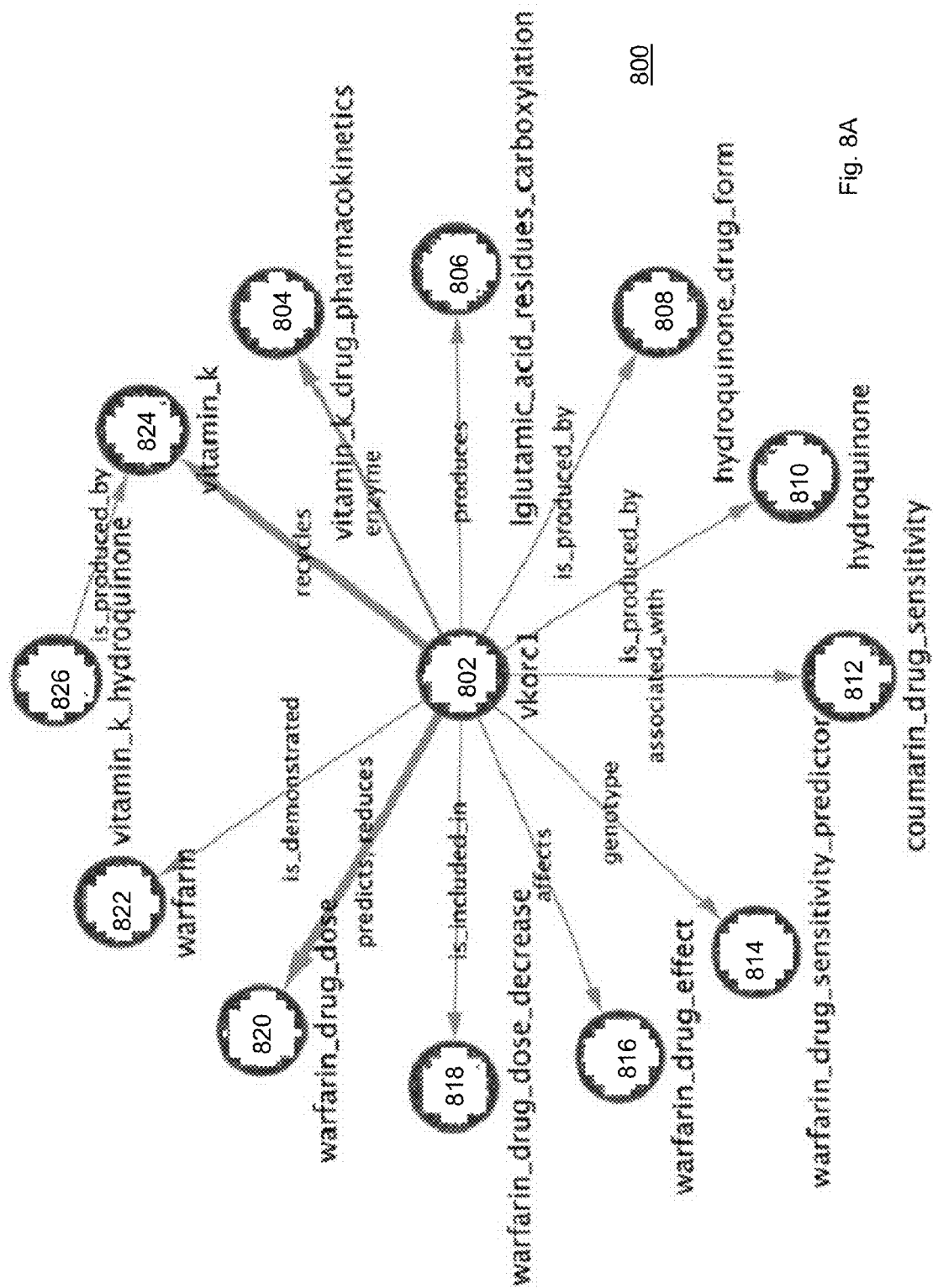
FIGS. 8A and 8B are examples of semantic networks extracted for the VKORC1 gene according to an embodiment of the present invention.

The resulting knowledge base is used to create PGx networks where nodes are PGx entities and edges are normalized relationships between these entities. These entities and relationships were mapped to common semantics as defined in the knowledge base. They are semantic networks. FIGS. 8A and B show such semantic networks related to the VKORC1 gene. For example, shown in FIG. 8A is the manner in which VKORC1 at node 802 is connected to PGx entities 804-826 through the edges of the network. FIG. 8A shows pharmacogenomics (PGx) relationships extracted from sentences that contain VKORC1 or one of its synonyms as a key entity. For example, it shows that VKORC1 802 predicts warfarin drug dose 820.

Figure 8B:

As a further example, FIG. 8B shows the manner in which variations of VKORC1 at nodes 850-856 are connected to PGx entities 858-890. Shown in FIG. 8B is a semantic network extracted for the VKOCR1 gene. FIG. 8B shows PGx relationships for entities that are modified by VKORC1 (e.g., VKORC1_haplotype 850, VKORC1_variant 854). For example, VKORC1 haplotypes 850 influence warfarin drug effect 858. Each node represents a PGx key or modified entity, e.g., warfarin 860 or warfarin_drug_effect 858. Edges represent relationships between these entities that are mentioned in MEDLINE abstracts. When several sentences mention a relationship between the same two entities, the edge is graphically wider and is labeled with the most frequent types of relationship. In an embodiment of the present invention, networks have been generated using Cytoscape v2.6.3 (http://www.cytoscape.org).

Figure 9:
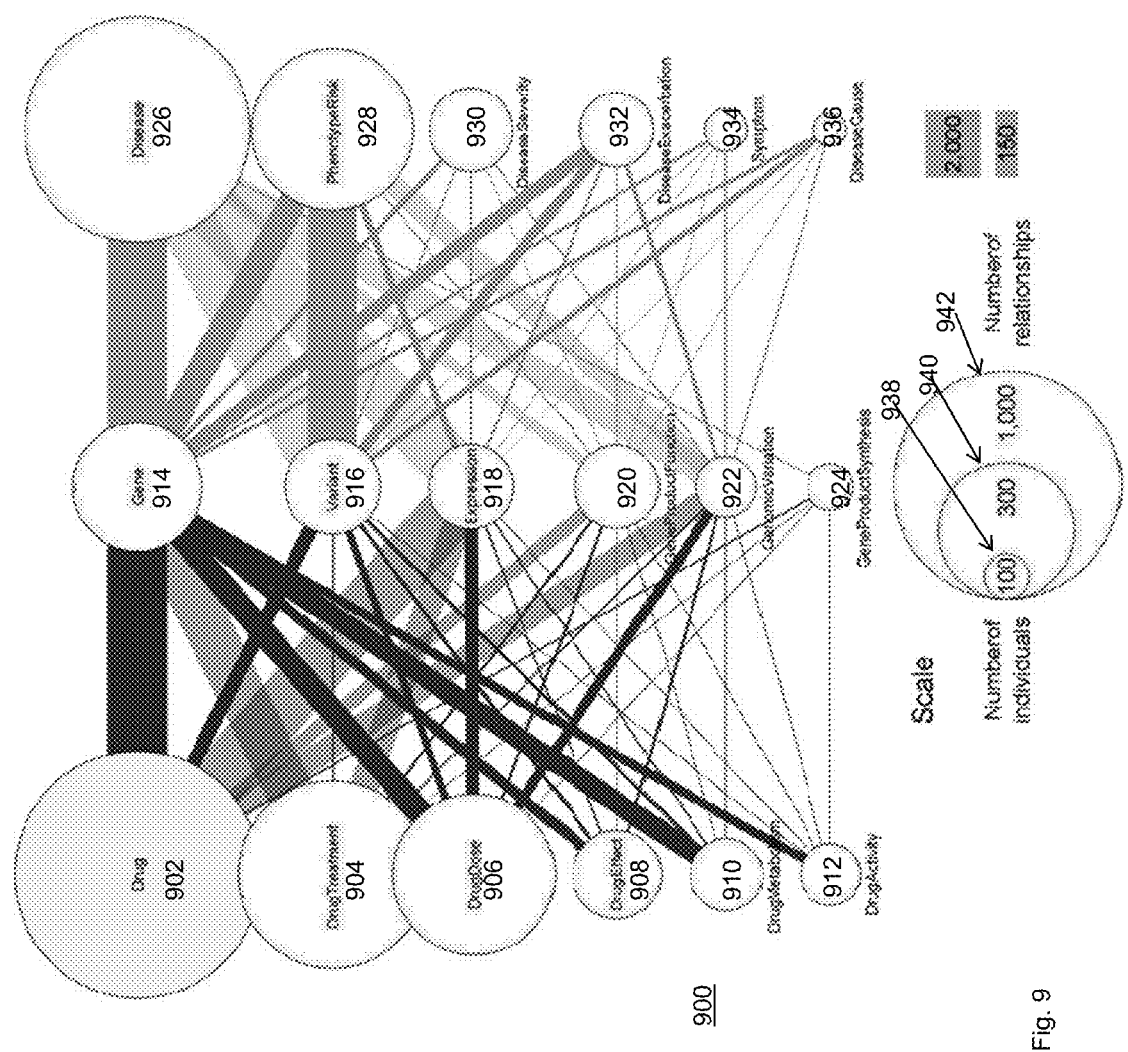
FIG. 9 is a summary of a pharmacogenomics (PGx) concept network according to an embodiment of the present invention.

FIG. 9 summarizes the number of entities in each entity class and the number of relationships between these and other entity types. As shown in network 900 of FIG. 9, nodes 902-936 represent concepts frequently appearing in PGx relationships. Their size is dependent on the number of instantiated PGx entities. Edges represent relationships between instances of two concepts. Their width is dependent on their number. This network has been built from the knowledgebase of 41,134 relationships extracted from the text of MEDLINE abstracts. For example, there are many statements in the PGx literature relating drugs to genes, and genes to diseases. There are somewhat less relating drug metabolism specifically to genomic variation. This network has been generated using Cytoscape v2.6.3 (http://www.cytoscape.org).

Discussion

At least two advantages certain embodiments of the present invention are: (1) the identification of both PGx key entities (genes, drugs, and phenotypes), as well as crucial and novel PGx entities modified by genes, drugs, and phenotypes, and (2) the association of extracted relationships with a normalized semantics, captured in an ontology. The syntactical structure of sentences allows the use of key entity lexicons to bootstrap the discovery and normalization of the modified entities critical to PGx and the ontology allows for recording these entities and recognizing them under very general textual conditions.

Embodiments of the present invention are flexible because they use syntactical patterns that are much more general than specific rules (e.g., x inhibits y). Such an embodiment is precise because it is based on the detection of relationships in natural language text, and does not depend upon co-occurrence of two recognized entities. A potential issue relating to syntactical parsing approaches compared to co-occurrence is potentially lower recall. Low recall is attenuated by large size of the corpus, which provides multiple opportunities to recognize a relationship. Precision may be improved by using full text. The recognition of named entities in sentences is based on string matching plus normalization techniques.

At this time, qualifiers that modulate the relationship itself such as negation, adverbs (e.g., not, highly, and hypothetically) are captured but not used. Another embodiment of the present invention would consider subcategorization frames in particular for ditransitive or caused-motion verbs (such as to transform for instance) that are reporting several relationships between one subject and multiple objects (e.g., x transforms y in z).

The presently described ontology was created and validated. Advantageously, the language used to describe PGx relationships degenerates to a small core of unique concepts in an embodiment of the invention. Other efforts for detecting synonyms use resources such as WordNet (http://wordnet.princeton.edu/), but this is not applicable to technical biological domains. Instead, domain experts were used to create acceptable synonym mappings. The decision to group words can be approximate, and some grouped words are not exact synonyms, such as SNP and allele. These similar words have been grouped to limit the number of distinct concepts in the ontology. The approach described here is completely applicable to other domains as would be understood by one of ordinary skill in the art. Human effort will be required to develop an ontology adapted to the domain if none is available.

CONCLUSION

An embodiment of the present invention has been disclosed as a method that uses the syntactical structure of sentences to extract biomedical relationships from text. Key pharmacogenomic entities (genes, drugs, and phenotypes) are used to bootstrap a process whereby other entities that are modified by these concepts are identified and stored in an ontology. The relationships used in pharmacogenomics literature are also captured and normalized, yielding a core set of 41,134 relationships that capture approximately 80% of extracted relationships in the text.

Embodiments of the present invention allow for automatically labeling a parsed sentence that provides a relationship between the key entities or the derivative modified entities—totaling more than 200 total entity types. A knowledge base of relationships from 17 million MEDLINE abstracts containing 87 million sentences was created. This knowledge base allows for the creation of semantically rich summaries of the relationships between genes, drugs, and phenotypes. By going beyond classic entity recognition for gene, drug and phenotype, and by not requiring prior enumeration of relationship types, a novel accurate and extensible approach to processing PGx text has been disclosed. This is a use of reasoning with an OWL ontology to integrate heterogeneous relationships extracted from text.

In other embodiments, the methods of the present invention described herein can be generalized to other domains of interest. For example, the methods of the present invention for extracting raw relationships from a free-form sentence can be applied to other domains. The normalization of the raw relationships uses a domain ontology. The methodology to create this ontology can also be applied to other domains. This method has been used to extract relationships between drugs, genes, and diseases from published literature. In other embodiments, the methods of the present invention can be used to extract drug-drug relationships (to predict adverse drug-drug interactions) or to extract drug-side-effect relationships to identify adverse reactions. The methods of the present invention can be also used to extract relationships from patent literature, web pages, the PhysiciansDesk Reference, FDA NDA documents, and other types of textual documents. Preferably, for example, (1) the documents should contain full sentences, (2) there should exist a list of entity lexicons, or seed terms of interest, such as drug names, gene names, disease names in the case of the pharmacogenomic domain, and (3) a domain ontology can be constructed for use in the normalization step.

It should be appreciated by those skilled in the art that the specific embodiments disclosed above may be readily utilized as a basis for modifying or designing processing algorithms or systems. It should also be appreciated by those skilled in the art that such modifications do not depart from the scope of the invention as set forth in the appended claims.

What is claimed is:

1. A computer implemented method for extracting pharmacogenomics relations from text, comprising:
   parsing a plurality of sentences into a plurality of parse trees;
   reducing the plurality of parse trees to include only parse trees of sentences where a plurality of seed terms occur within a same clause, wherein seed terms are identified from a lexicon comprising pharmacogenomics entities;
   transforming the reduced plurality of parse trees into a plurality of dependency graphs;
   identifying a plurality of entities from the plurality of seed terms for each dependency graph, said identifying comprising:
      identifying at least one modified entity by traversing a particular dependency graph of the plurality of dependency graphs in order to identify a core term modified by a seed term of the plurality of seed terms as the modified entity; and
      identifying seed terms from the particular dependency graph that do not modify a core term as key entities;
   identifying extracting a plurality of relations between the identified plurality of entities from the plurality of dependency graphs, wherein each relation of the plurality of relations comprises at least first and second entities of the plurality of entities of a particular dependency graph and a relationship between the first and second entities that is identified by traversing edges within the particular dependency graph between the first and second entities to reach a same particular verb, wherein at least one of the first and second entities is a modified entity;
   constructing an ontology based on relative frequencies of the plurality of relations and of entities of the plurality of entities;
   normalizing the entities and the relationships within the identified plurality of relations according to the constructed ontology; and
   storing the normalized plurality of relations and normalized seed terms in a memory of at least one computer system.

2. The method of claim 1, wherein the plurality of sentences includes pharmacogenomics information.

3. The method of claim 1, further comprising extracting the plurality of sentences from articles, where an article is a file containing a text document.

4. The method of claim 3, wherein:
   an article is a file containing a structured text document including an abstract; and
   the plurality of sentences is extracted from abstracts of the articles.

5. The method of claim 1, wherein the dependency graphs provide a syntactical structure for the plurality of sentences.

6. The method of claim 1, wherein the relations describe pharmacogenomics relationships between pharmacogenomics entities.

7. The method of claim 1, wherein the ontology is an ontology of pharmacogenomics relationships.

8. The method of claim 1, further comprising mapping the plurality of relations to the ontology.

9. The method of claim 1, further comprising creating a network of pharmacogenomics entities and their relations.

10. The method of claim 1, wherein the ontology is hierarchical.

11. The method of claim 1, wherein the plurality of sentences includes pharmacogenomics information, where pharmacogenomics information includes at least one relationship between a genomic variation and a drug response phenotype.

12. The method of claim 1, wherein key entities are genes, drugs, and phenotypes, and modified entities comprise a core term modified by at least one of a gene, a drug, and a phenotype.

13. The method of claim 1, wherein each relationship of the plurality of relationships is binary and relates at least one subject to at least one object.

14. The method of claim 1, wherein the ontology is an ontology of pharmacogenomics relationships, where a pharmacogenomics relationship is binary and relates at least one subject to at least one object.

15. The method of claim 1, wherein the ontology is hierarchical, where lists of raw relationships extracted from data graphs are sorted by frequency with respect to the most frequent relationship types and the most frequent modified entities modified by genes, drugs and phenotypes.

16. The method of claim 1, where the ontology is hierarchical, where a list of raw relationships extracted from dependency graphs is organized into role and concept hierarchies,
where a role is a binary relation associated with relationship synonyms, and
where a concept is a set of synonyms for seed terms that are used to modify core terms in a modified entity.

17. A non-transitory computer-readable medium including instructions that, when executed by a processing unit, cause the processing unit to extract pharmacogenomics relations from text, by performing the steps of:
parsing a plurality of sentences into a plurality of parse trees;
reducing the plurality of parse trees to include only parse trees of sentences where a plurality of seed terms occur within a same clause, wherein seed terms are identified from a lexicon comprising pharmacogenomics entities;
transforming the reduced plurality of parse trees into a plurality of dependency graphs;
identifying a plurality of entities from the plurality of seed terms for each dependency graph, said identifying comprising:
identifying at least one modified entity by traversing a particular dependency graph of the plurality of dependency graphs in order to identify a core term modified by a seed term of the plurality of seed terms as the modified entity; and
identifying seed terms from the particular dependency graph that do not modify a core term as key entities;
identifying a plurality of relations between the identified plurality of entities from the plurality of dependency graphs, wherein each relation of the plurality of relations comprises at least first and second entities of the plurality of entities of a particular dependency graph and a relationship between the first and second entities that is identified by traversing edges within the particular dependency graph between the first and second entities to reach a same particular verb, wherein at least one of the first and second entities is a modified entity;
constructing an ontology based on relative frequencies of the plurality of relations and of entities of the plurality of entities;
normalizing the entities and the relationships within the identified plurality of relations according to the constructed ontology; and
storing the normalized plurality of relations and normalized seed terms in a memory of at least one computer system.

18. The non-transitory computer-readable medium of claim 17, wherein the plurality of sentences includes pharmacogenomics information.

19. The non-transitory computer-readable medium of claim 17, further comprising extracting the plurality of sentences from articles, where an article is a file containing text documents.

20. The non-transitory computer-readable medium of claim 19, wherein:
an article is a file containing a structured text document including an abstract; and
the plurality of sentences is extracted from abstracts of the articles.

21. The non-transitory computer-readable medium of claim 17, wherein the dependency graphs provide a syntactical structure for the plurality of sentences.

22. The non-transitory computer-readable medium of claim 17, wherein the relations describe pharmacogenomics relationships between pharmacogenomics entities.

23. The non-transitory computer-readable medium of claim 17, wherein the ontology is an ontology of pharmacogenomics relationships.

24. The non-transitory computer-readable medium of claim 17, further comprising mapping the plurality of relations to the ontology.

25. The non-transitory computer-readable medium of claim 17, further comprising creating a network of pharmacogenomics entities and their relations.

26. The non-transitory computer-readable medium of claim 17, wherein the ontology is hierarchical.

27. The non-transitory computer-readable medium of claim 17, wherein the plurality of sentences includes pharmacogenomics information, where pharmacogenomics information includes at least one relationship between a genomic variation and a drug response phenotype.

28. The non-transitory computer-readable medium of claim 17, wherein key entities are genes, drugs, and phenotypes, and modified entities comprise a core term modified by at least one of a gene, a drug, and a phenotype.

29. The non-transitory computer-readable medium of claim 17, wherein each relationship of the plurality of relationships is binary and relates at least one subject to at least one object.

30. The non-transitory computer-readable medium of claim 17, wherein the ontology is an ontology of pharmacogenomics relationships, where a pharmacogenomics relationship is binary and relates at least one subject to at least one object.

31. The non-transitory computer-readable medium of claim 17, wherein the ontology is hierarchical, where lists of raw relationships extracted from data graphs are sorted by frequency with respect to the most frequent relationship types and the most frequent modified entities modified by genes, drugs and phenotypes.

32. The non-transitory computer-readable medium of claim 17, where the ontology is hierarchical, where a list of raw relationships extracted from dependency graphs is organized into role and concept hierarchies,
where a role is a binary relation associated with relationship synonyms, and where a concept is a set of synonyms for seed terms that are used to modify core terms in a modified entity.

33. A computing device comprising:
a data bus;
a memory unit coupled to the data bus;
a processing unit coupled to the data bus and configured to
 parse a plurality of sentences into a plurality of parse trees;
 reduce the plurality of parse trees to include only parse trees of sentences where a plurality of seed terms occur within a same clause, wherein seed terms are identified from a lexicon comprising pharmacogenomic entities;
 transform the reduced plurality of parse trees into dependency graphs;
 identify a plurality of entities from the plurality of seed terms for each dependency graph, said processing unit configured to identify the plurality of entities by:
  identifying at least one modified entity by traversing a particular dependency graph of the plurality of dependency graphs in order to identify a core term modified by a seed term of the plurality of seed terms as the modified entity; and
  identifying seed terms from the particular dependency graph that do not modify a core term as key entities;
 identify a plurality of relations between the identified plurality of entities from the dependency graphs, wherein each relation of the plurality of relations comprises at least first and second entities of the plurality of entities of a particular dependency graph and a relationship between the first and second entities that is identified by traversing edges within the particular dependency graph between the first and second entities to reach a same particular verb, wherein at least one of the first and second entities is a modified entity;
 construct an ontology based on relative frequencies of the plurality of relations and of entities of the plurality of entities;
 normalize the entities and the relationships within the identified plurality of relations according to the constructed ontology; and
 store the normalized plurality of relations and normalized seed terms in a memory of at least one computer system.

* * * * *